US007373596B2

(12) United States Patent
Hu et al.

(10) Patent No.: US 7,373,596 B2
(45) Date of Patent: *May 13, 2008

(54) PRECISE UML MODELING FRAMEWORK OF THE DICOM INFORMATION MODEL

(75) Inventors: Jingkun Hu, Pleasanton, CA (US); Kwok Pun Lee, Ossining, NY (US); Alfredo Tirado-Ramos, Amsterdam (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 611 days.

This patent is subject to a terminal disclaimer.

(21) Appl. No.: 10/210,520

(22) Filed: Aug. 1, 2002

(65) Prior Publication Data

US 2004/0025110 A1 Feb. 5, 2004

(51) Int. Cl.
*G06F 15/00* (2006.01)
*G06F 17/00* (2006.01)
(52) U.S. Cl. .................................. 715/513; 715/523
(58) Field of Classification Search ................ 715/513, 715/523
See application file for complete search history.

(56) References Cited

U.S. PATENT DOCUMENTS

| 6,353,445 | B1 * | 3/2002 | Babula et al. ............... 715/733 |
| 6,725,231 | B2 * | 4/2004 | Hu et al. ..................... 707/102 |
| 6,775,834 | B2 * | 8/2004 | Bidarahalli et al. .......... 719/328 |
| 6,874,146 | B1 * | 3/2005 | Iyengar ....................... 719/313 |
| 6,950,985 | B2 * | 9/2005 | Lee ............................ 715/513 |
| 2002/0023172 | A1 * | 2/2002 | Gendron et al. ............. 709/238 |
| 2002/0055917 | A1 * | 5/2002 | Muraca .......................... 707/1 |
| 2002/0124119 | A1 * | 9/2002 | Bidarahalli et al. .......... 709/328 |
| 2002/0143727 | A1 * | 10/2002 | Hu et al. ....................... 707/1 |
| 2002/0143824 | A1 * | 10/2002 | Lee et al. ................... 707/523 |
| 2004/0025110 | A1 * | 2/2004 | Hu ............................. 715/500 |
| 2004/0205563 | A1 * | 10/2004 | Lee ............................ 715/513 |

OTHER PUBLICATIONS

W. Dean Bidgood, Jr., M.D., M.S., SR Documentation Model, Jun. 25, 1999.*
DICOM Standards Committee, Digital Imaging and Communications in Medicine (DICOM), Apr. 6, 2000.*
Tirado-Ramos, Alfredo, Jingkun Hu, and K.P. Lee, "Information Object Definition-based Unified Modeling Language Representation of DICOM Structured Reporting", Journal of the American Medical Informatics Association, vol. 9, No. 1, pp. 63-72, Jan./Feb. 2002.*
A. Tirado-Ramos, "UML Model and XML Representation of Digital . . . ", U.S. Appl. No. 09/686,401, filed Oct. 10, 2000, Pending.

* cited by examiner

Primary Examiner—Rachna Singh

(57) ABSTRACT

A method for mapping a DICOM document into a UML document is disclosed and claimed by this invention. The method includes mapping each DICOM Information Entity in the DICOM document into a corresponding UML class in the UML document, mapping each DICOM IOD Module in the DICOM document into a corresponding UML class in the UML document, mapping each DICOM Macro in the DICOM document into a corresponding UML class in the UML document, and mapping each DICOM Attribute in the DICOM document into a corresponding UML attribute in the UML document. It also includes a UML profile for DICOM information model which guides the UML modeling for all the DICOM IODs. It can also guide the genertion of XML schemas and DTDs from UML models based on this profile.

12 Claims, 33 Drawing Sheets

```
                  « DICOMModule »
                    PatientModule
« XSDelement » patients_name : PatientsName
« XSDelement » patient_id : PatientId
« XSDelement » patients_birth_date : PatientBirthDate
« XSDelement » patients_sex : PatientsSex
« XSDelement » patients_birth_time [0..1] : PatientBirthTime
« XSDelement » other_patient_Ids [0..1] : OtherPatientIds
« XSDelement » other_patient_names [0..1] : OtherPatientNames
« XSDelement » ethnic_group [0..1] : EthnicGroup
« XSDelement » patient_comments [0..1] : PatientComments
« XSDelement » referenced_patient_seq [0..1] : ReferencedPatientSeq
```

FIG. 11

```
                  « DICOMMacro »
                  NumericMeasurement
measured_value_seq [0..1] : MeasuredValueSeq
codeId = (0040,A300)
codeMeaning = Measured Value Sequence
nillable = true
```

FIG. 12

```
                  « DICOMSequence »
                  ReferencedPatientSeq
reference_patient_seq_item : ReferencesSOPUID
codeId = (0008,1120)
codeMeaning = Referenced patient Sequence
```
                              ↓
                    « DICOMMacro »
                    ReferencedSOPUID

FIG. 13

| FIG. 27A | FIG. 27B |

FIG. 27

| FIG. 28A | FIG. 28B |

FIG. 28

PRECISE UML MODELING FRAMEWORK OF THE DICOM INFORMATION MODEL

BACKGROUND OF THE INVENTION

The present invention relates to the Digital Imaging and Communications in Medicine (DICOM) standard, and more particularly relates to a standard representation of DICOM in the unified modeling language (UML), i.e., a UML profile for DICOM.

The Digital Imaging and Communications in Medicine (DICOM) standard is a detailed specification that describes a means for formatting and exchanging images, and associated information. relies on standard communication protocols and addresses the communication and viewing of images from such modalities such as CT, MR, Ultrasound, Nuclear medicine, Digital Cardiology, Angiography, RF equipment and Radiation Therapy devices and systems. Extensions are being developed to include modalities with visible light sources such as Ophthalmology, Microscopy for Pathology applications, as well as Endoscopy. It also allows the exchange of patient demographic data, exam status and scheduling information. The rapid adoption of DICOM by the medical imaging industry is opening new opportunities for healthcare organizations to increase the quality and cost effectiveness of patient care.

DICOM has an information model defining a set of Information Object Definitions (IODs) which provide an abstract definition of real-world objects applicable to communication of digital medical information. For each IOD, DICOM specifies any necessary information for the semantic description of the IOD, relationships to associated real-world objects relevant to the IOD and attributes which describe the characteristics of the IOD. Each IOD, moreover, is defined as a set of tables based on the entity-relationship (E-R) scheme. The problem is that IODs are not machine-readable and not easy to capture and follow for non-DICOM literates. This acts as a barrier to communication between information architects and software developers from different domains.

OBJECTS AND SUMMARY OF THE INVENTION

Hence, it is an object of this invention to provide a standard model or template for the Digital Imaging Communications in Medicine (DICOM) using UML.

It is another object of the invention to provide a standard DICOM model or template which may be used to guide UML modeling for DICOM to improve communication among the information architects and developers from medical imaging domains and software industry domains.

It is still another object of the invention to generate a UML document from DICOM Information Object Definitions (IODs).

It is still another object of the invention to generate a UML document based on a UML model or template derived from DICOM IODsc It is still another object of the invention to provide means and method to generate Document Type Definitions (DTDs) or XML schemas from UML documents.

It is yet another object of this invention to provide a UML profile for DICOM which is machine readable and therefore readily communicable within various medical domains.

It is yet another object of this invention to provide a means and method to build UML models for the future DICOM IODs, Modules, Macros, or Attributes.

These objects of the invention (and others) are achieved by providing a modeling technique to convert DICOM information from the DICOM relational model into an object-oriented representation. A methodology is presented for converting the DICOM specification into a UML-based object-oriented representation of the specification, and for converting DICOM reports into UML-compatible representations. This methodology for representing the DICOM specification provides a clear and comprehensive view of's semantically rich framework, its structures and constructs. By providing a mapping between DICOM and UML, developers, analysts and system architects will be better able to understand the DICOM specification, and better able to define and develop DICOM-aware applications.

The inventions disclosed herein set forth a unique UML profile for DICOM based on the standard stereotypes of UML. Using the inventive a UML profile, the DICOM constraints can be precisely represented in object models, realizing a precise representation of the DICOM information model, and UML documents translated from DICOM-defined documents may be generated.

The benefit of a common and precise representation of the DICOM information model is the ability to communicate between DICOM and non-DICOM literates for various reasons, including that such a model is machine-readable and can help to automate the development of DICOM applications. The DICOM information model or template is utilized to guide UML modeling for DICOM information object definitions, and to translate between DICOM documents and UML documents.

BRIEF DESCRIPTION OF THE DRAWING FIGURES

Figure 6:
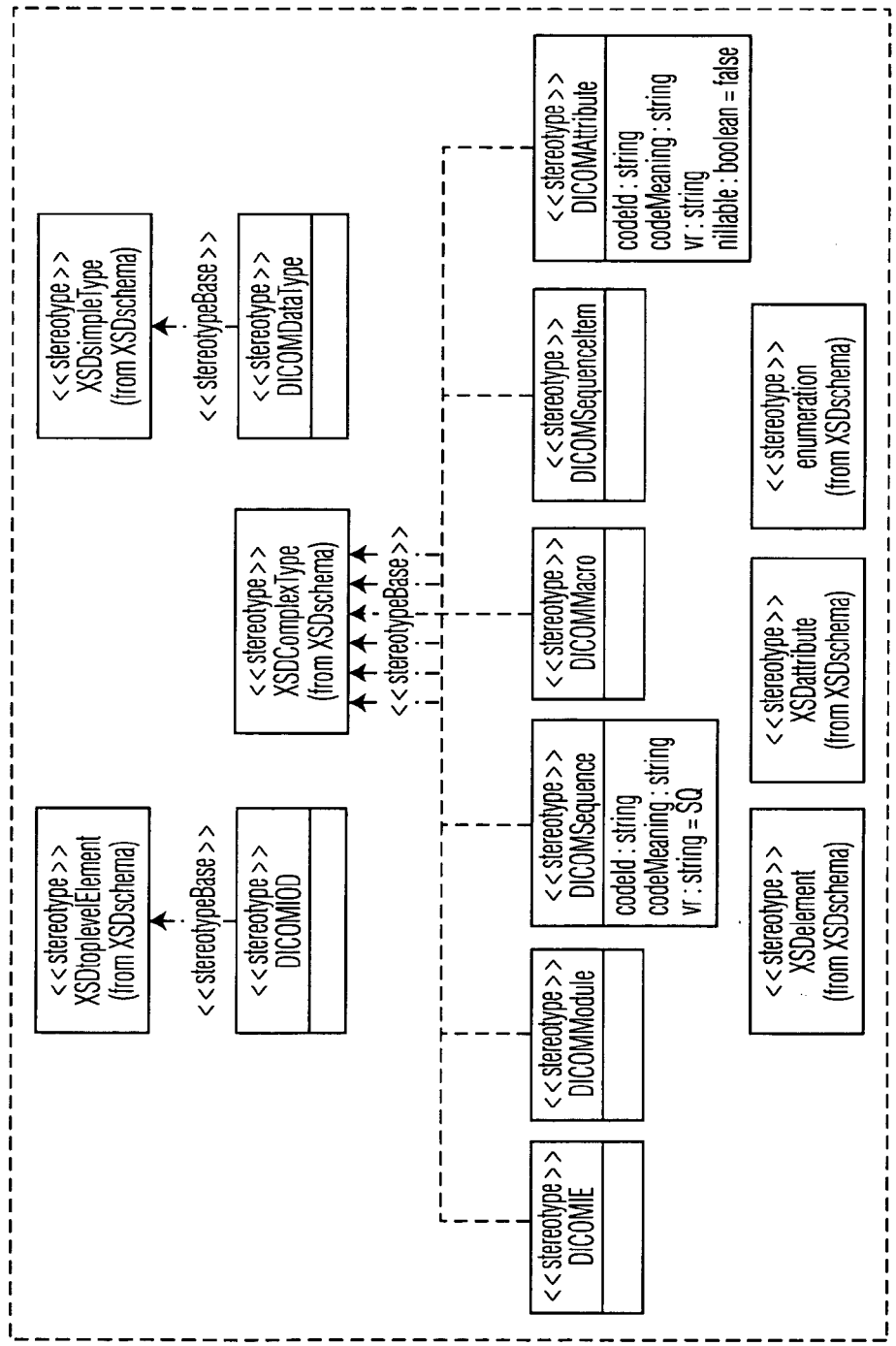
Figure 7:
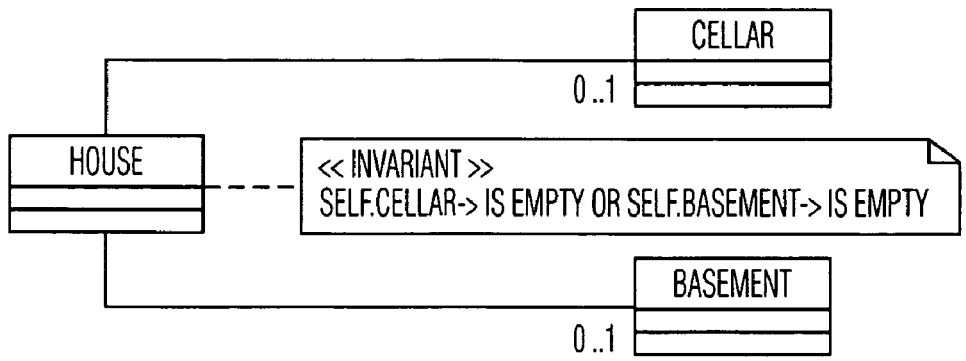
Figure 8:
Figure 9:
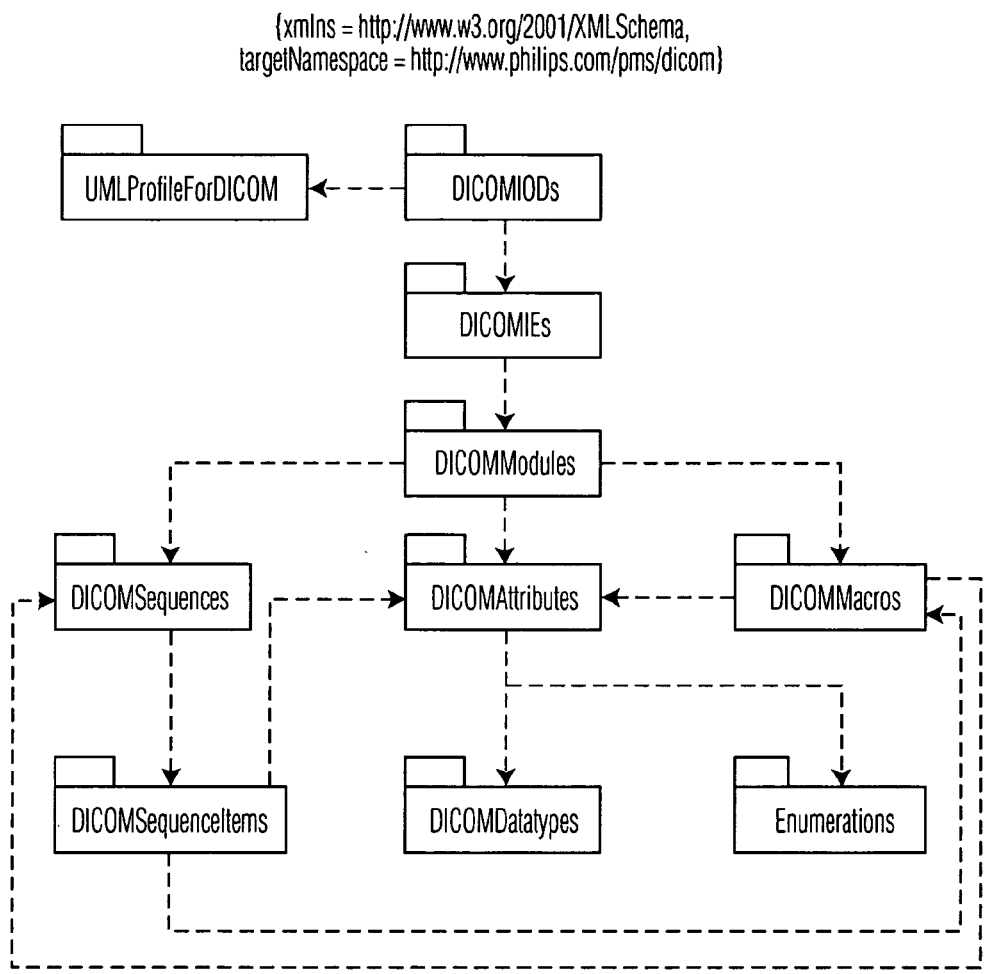
Figure 10:
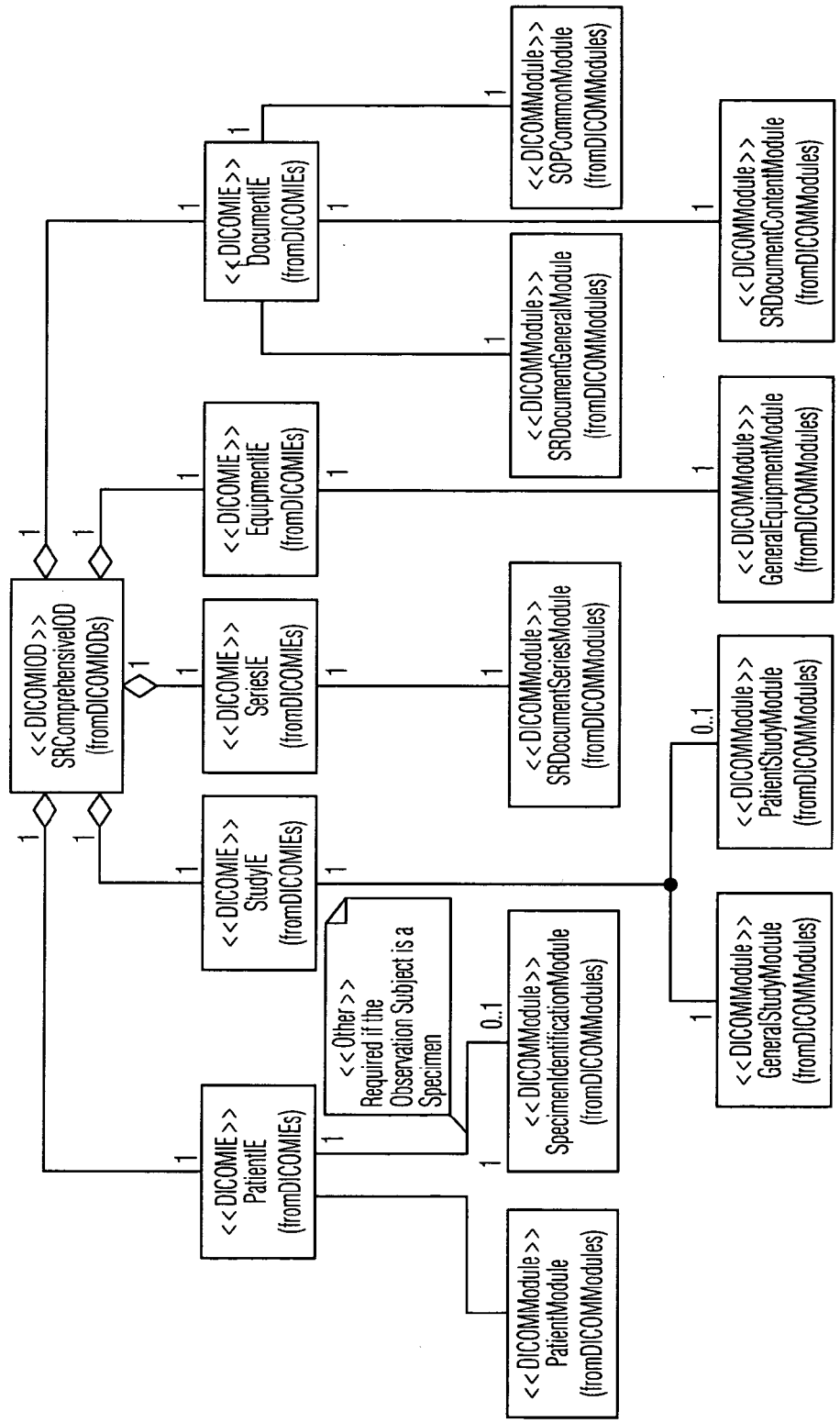
Figure 14:
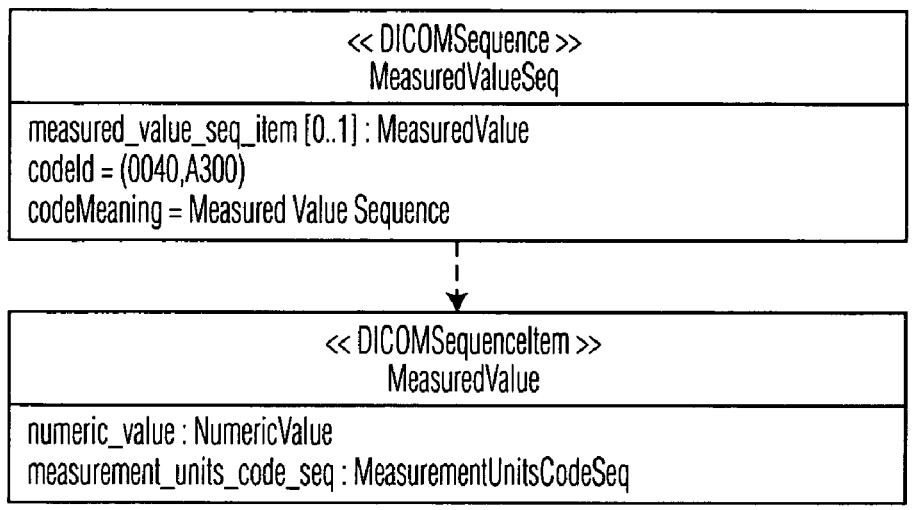
Figure 15:
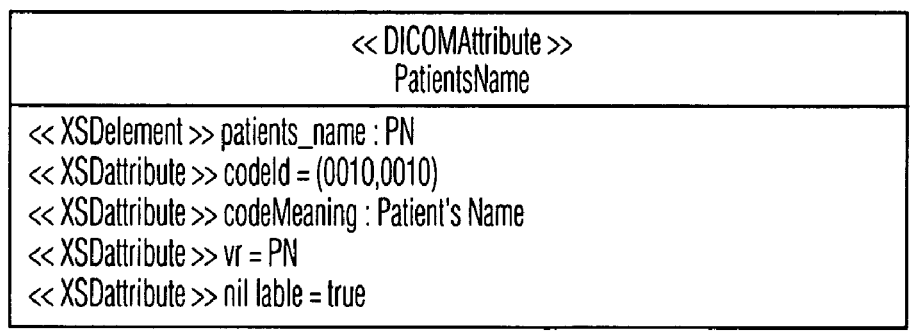
Figure 16:
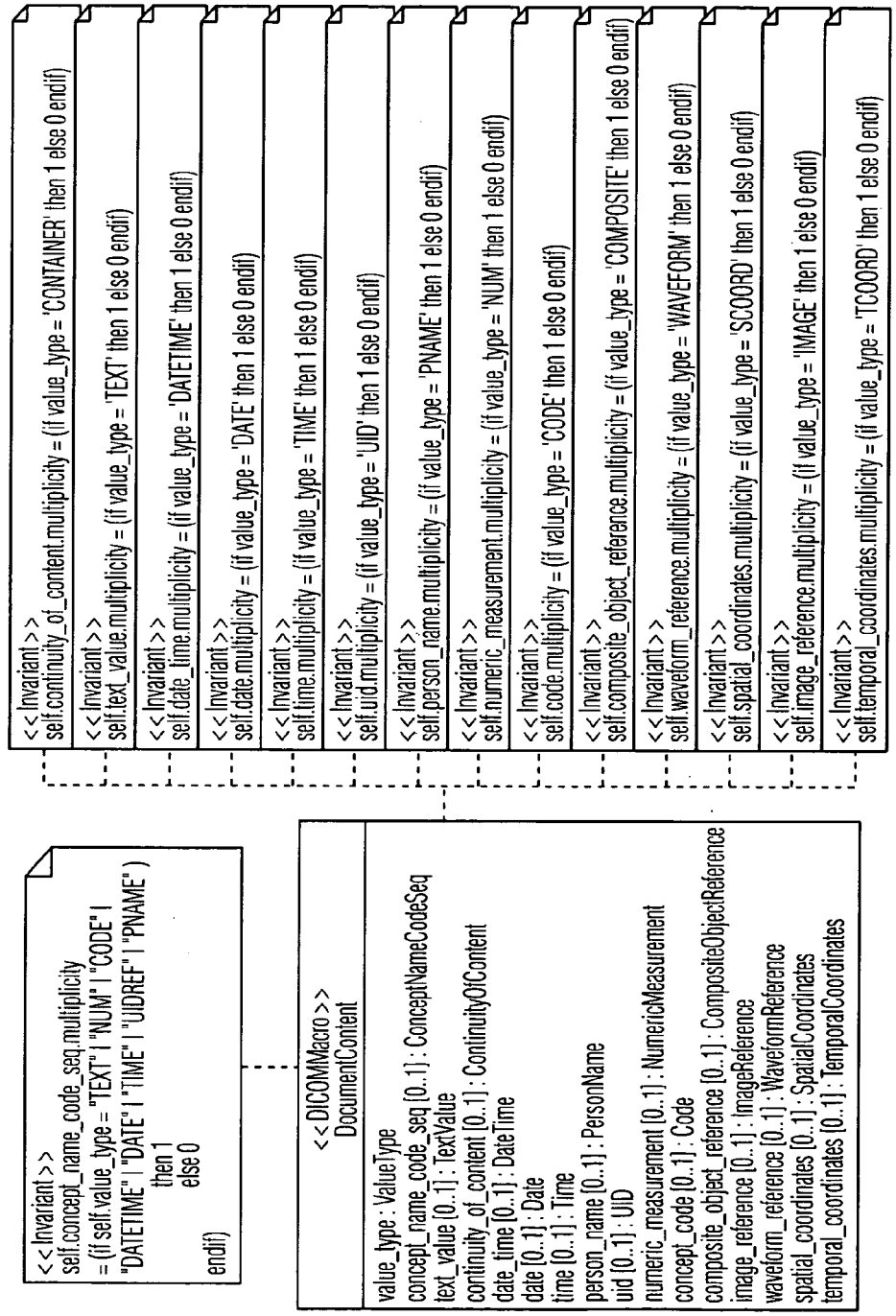
Figures 17, 18:
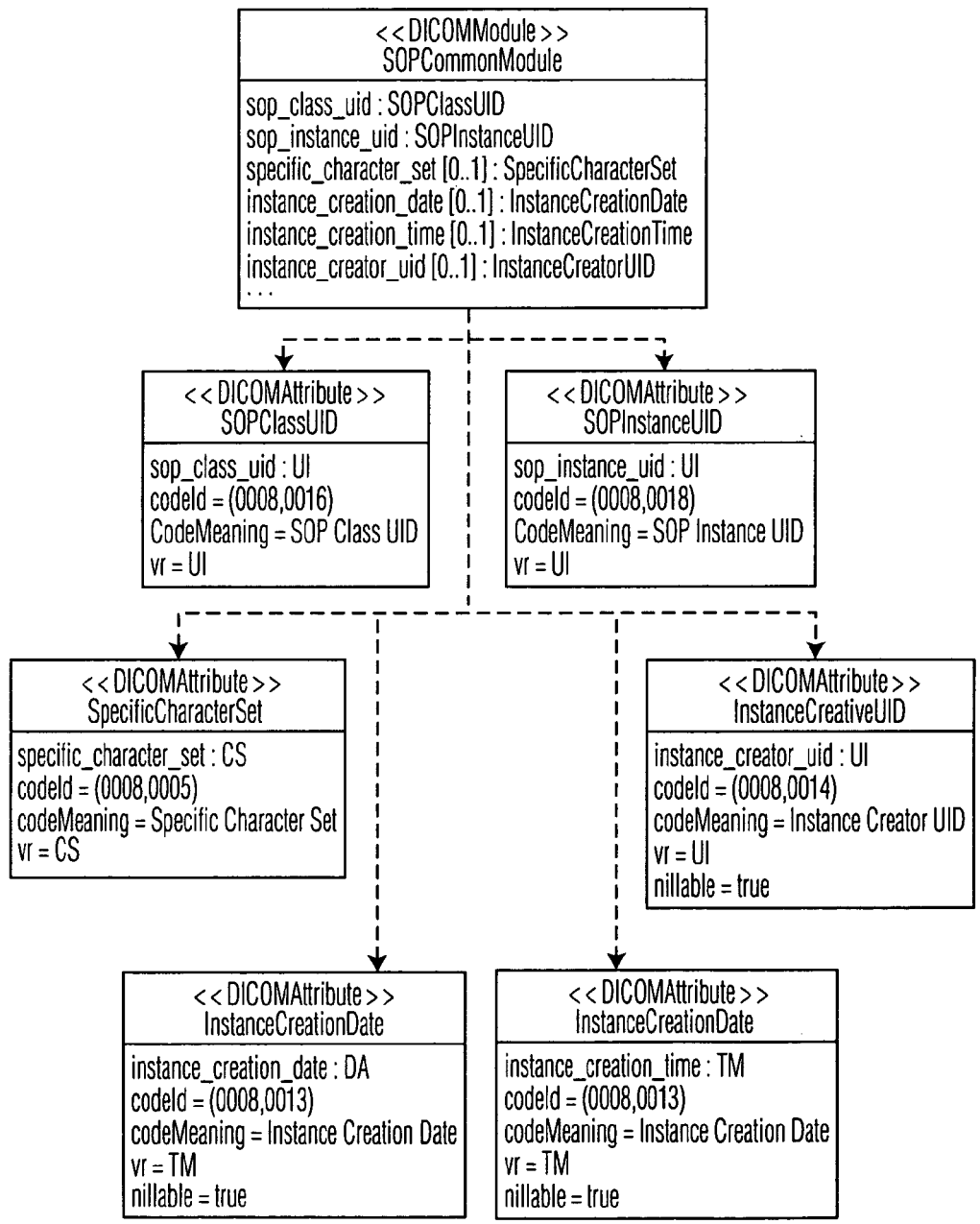
Figures 19, 20, 21:
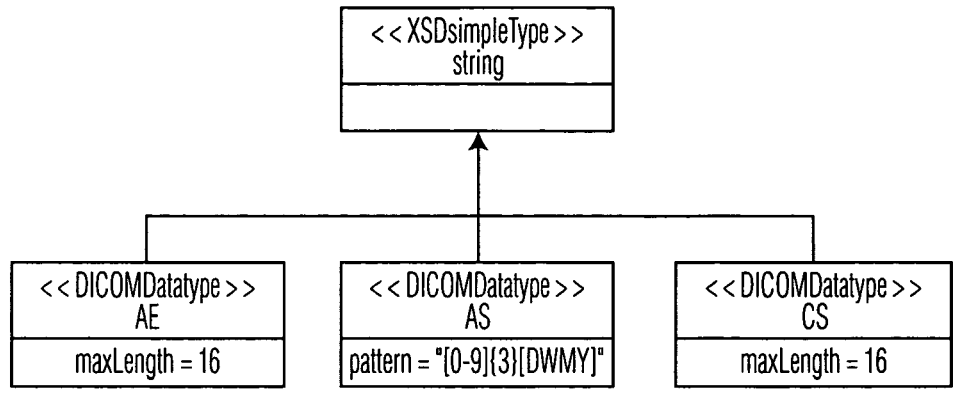
Figure 22:
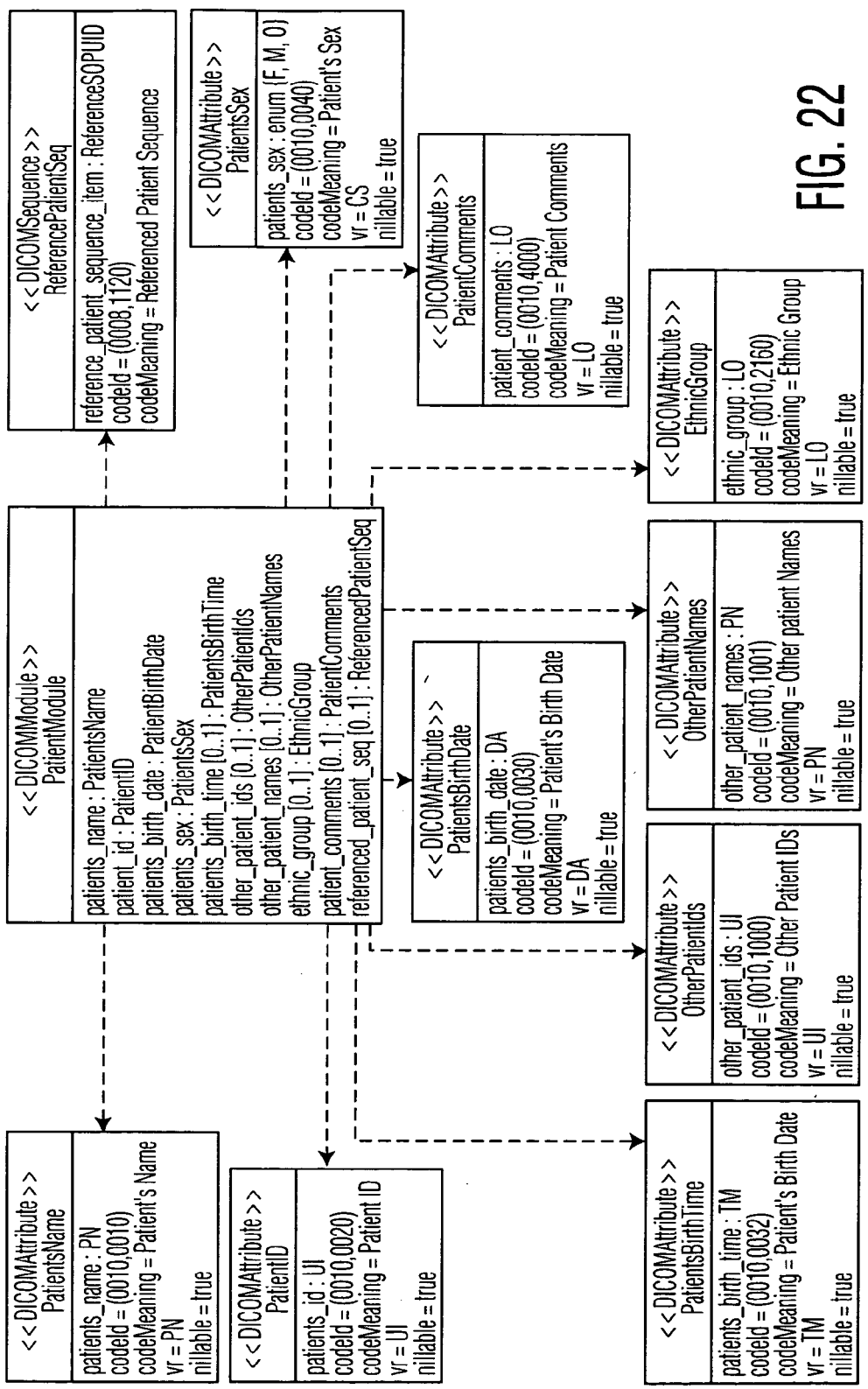
Figure 23:
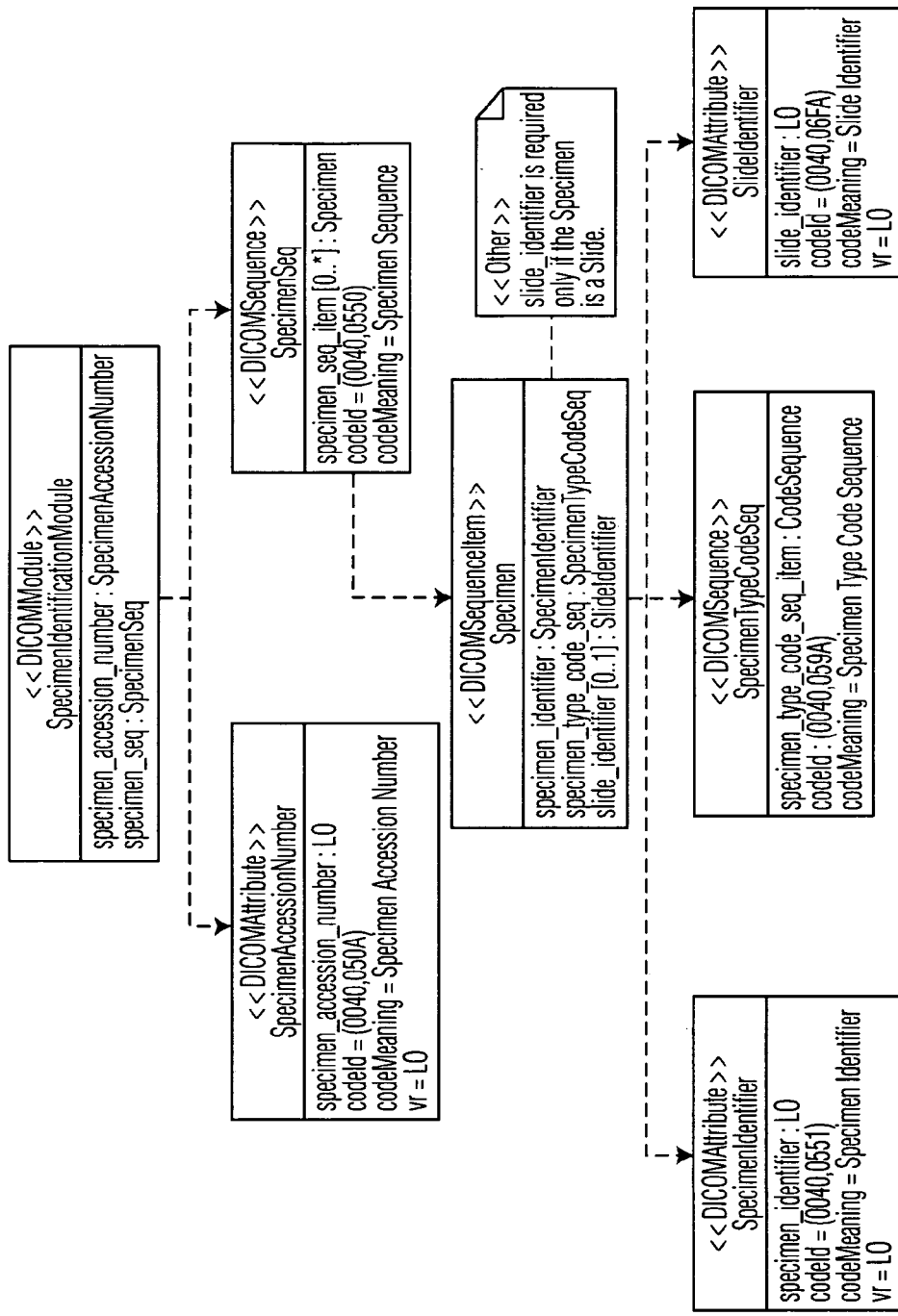
Figure 24:
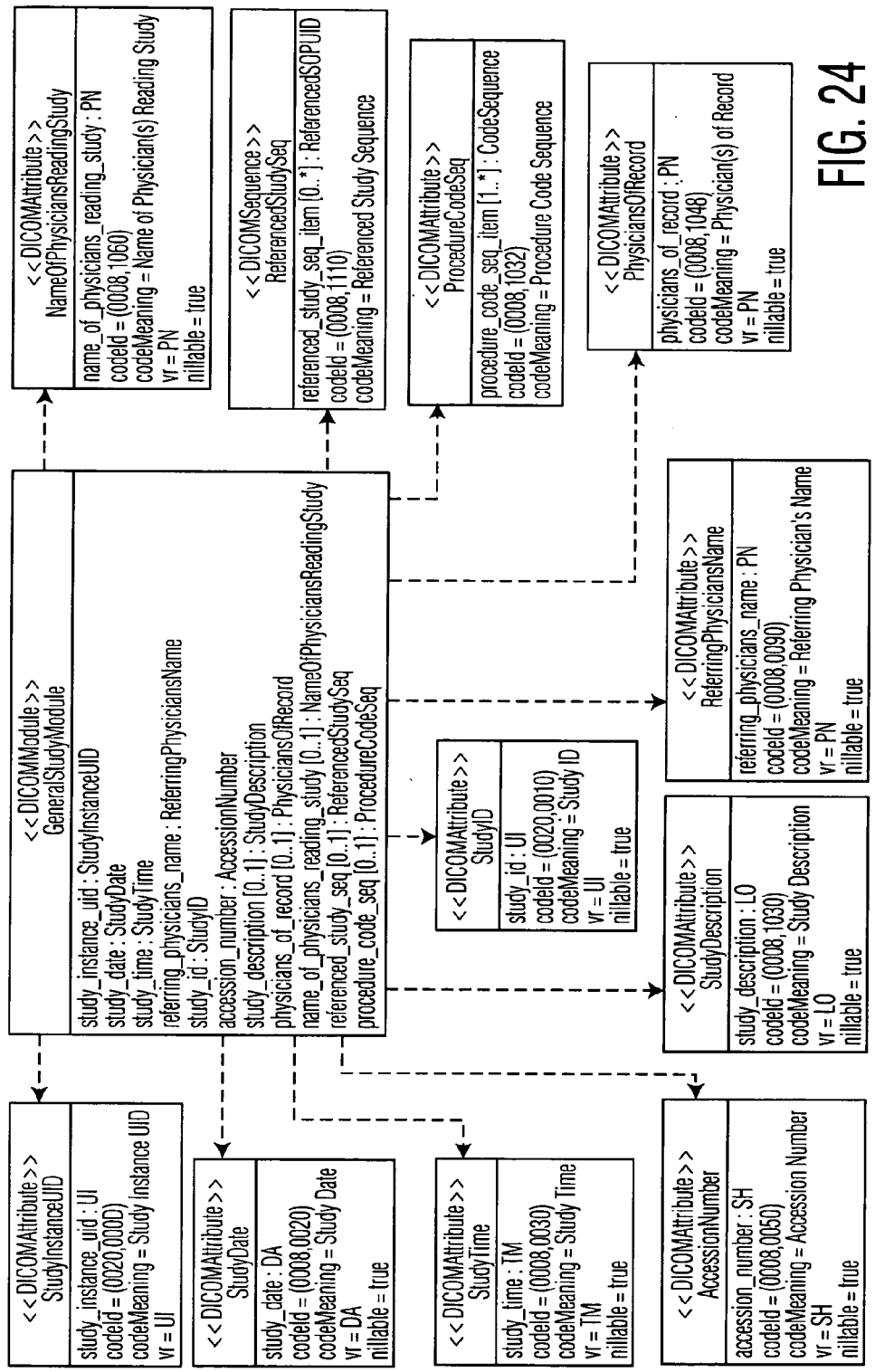
Figure 25:
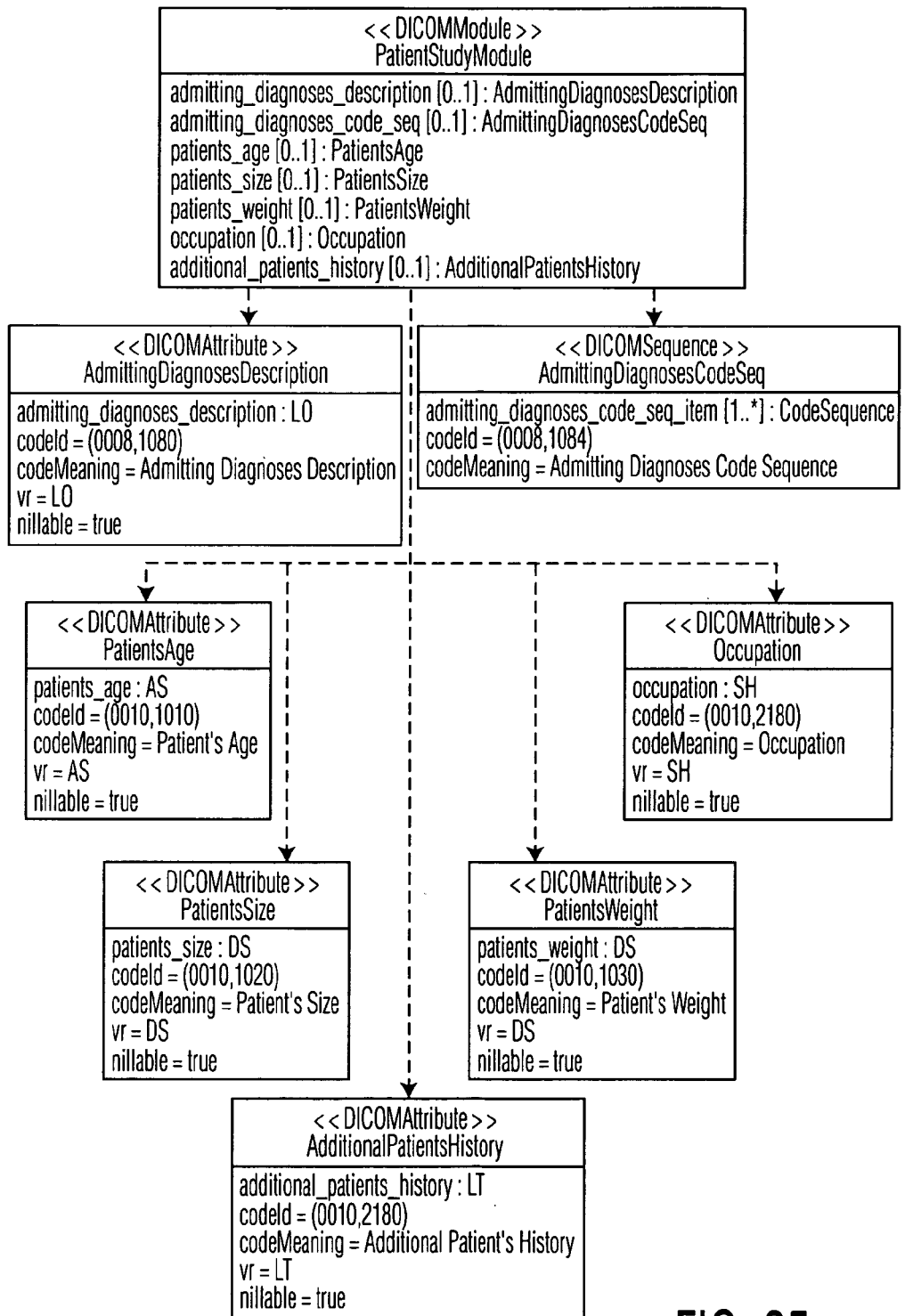
Figure 26:
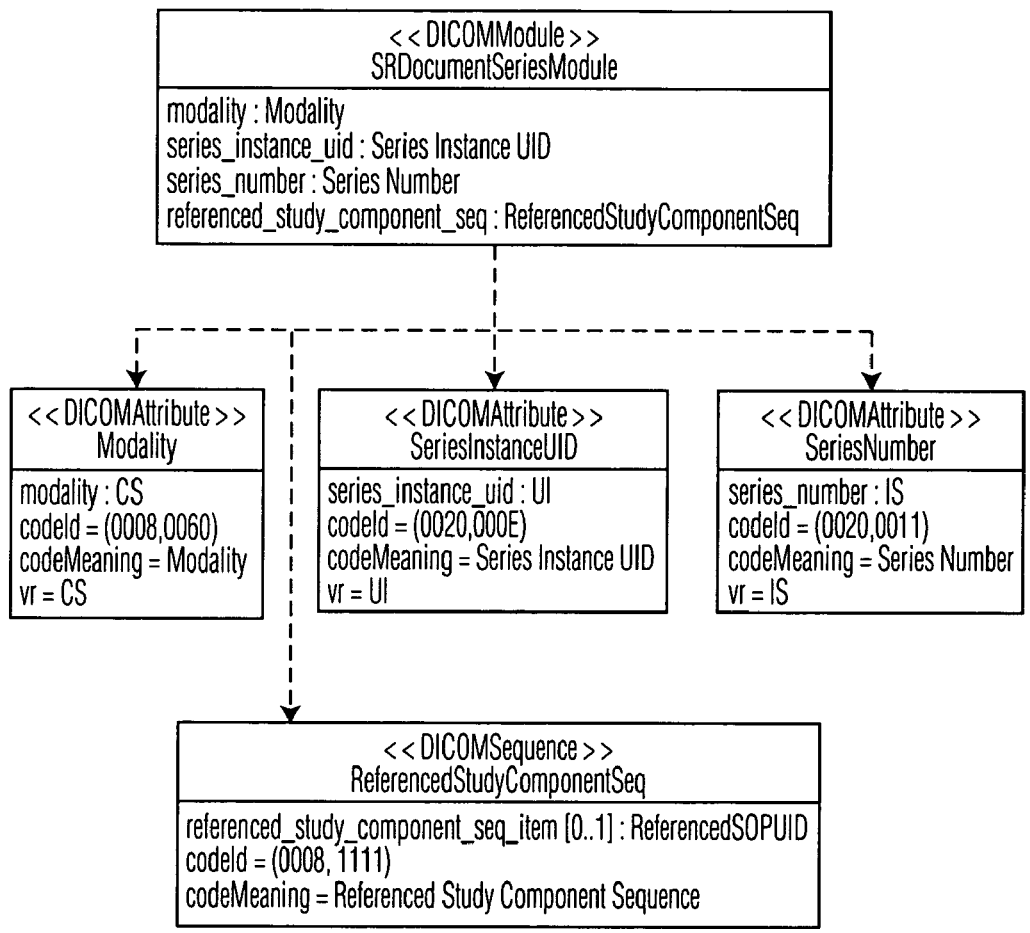
Figure 27A:
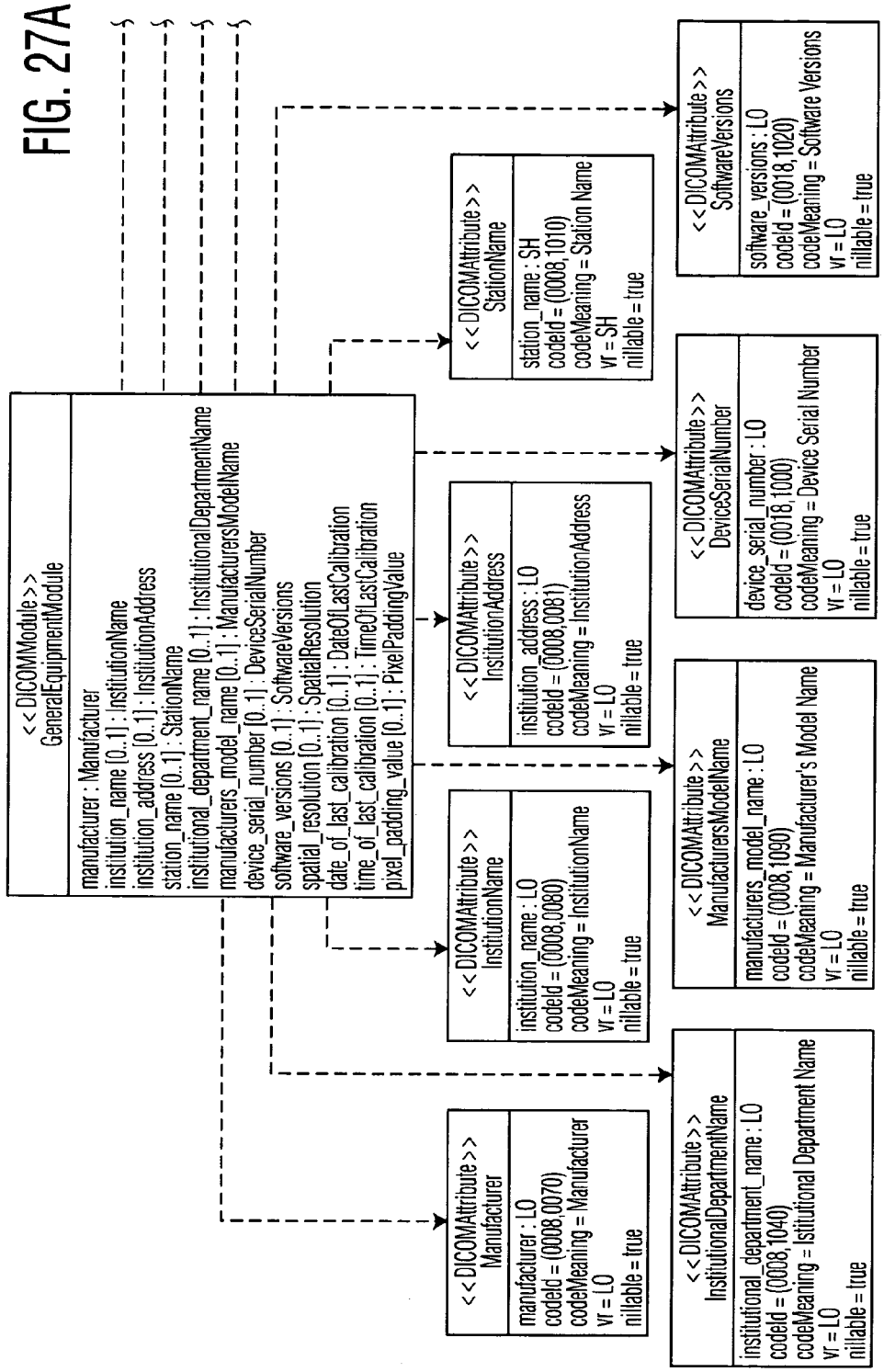
Figure 27B:
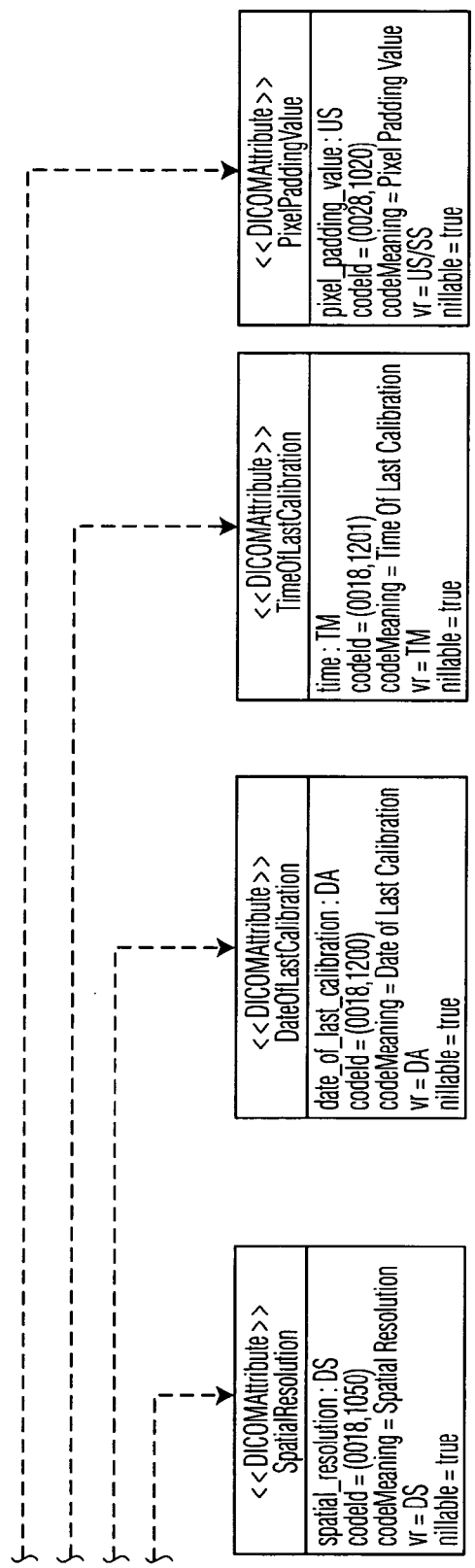
Figure 28A:
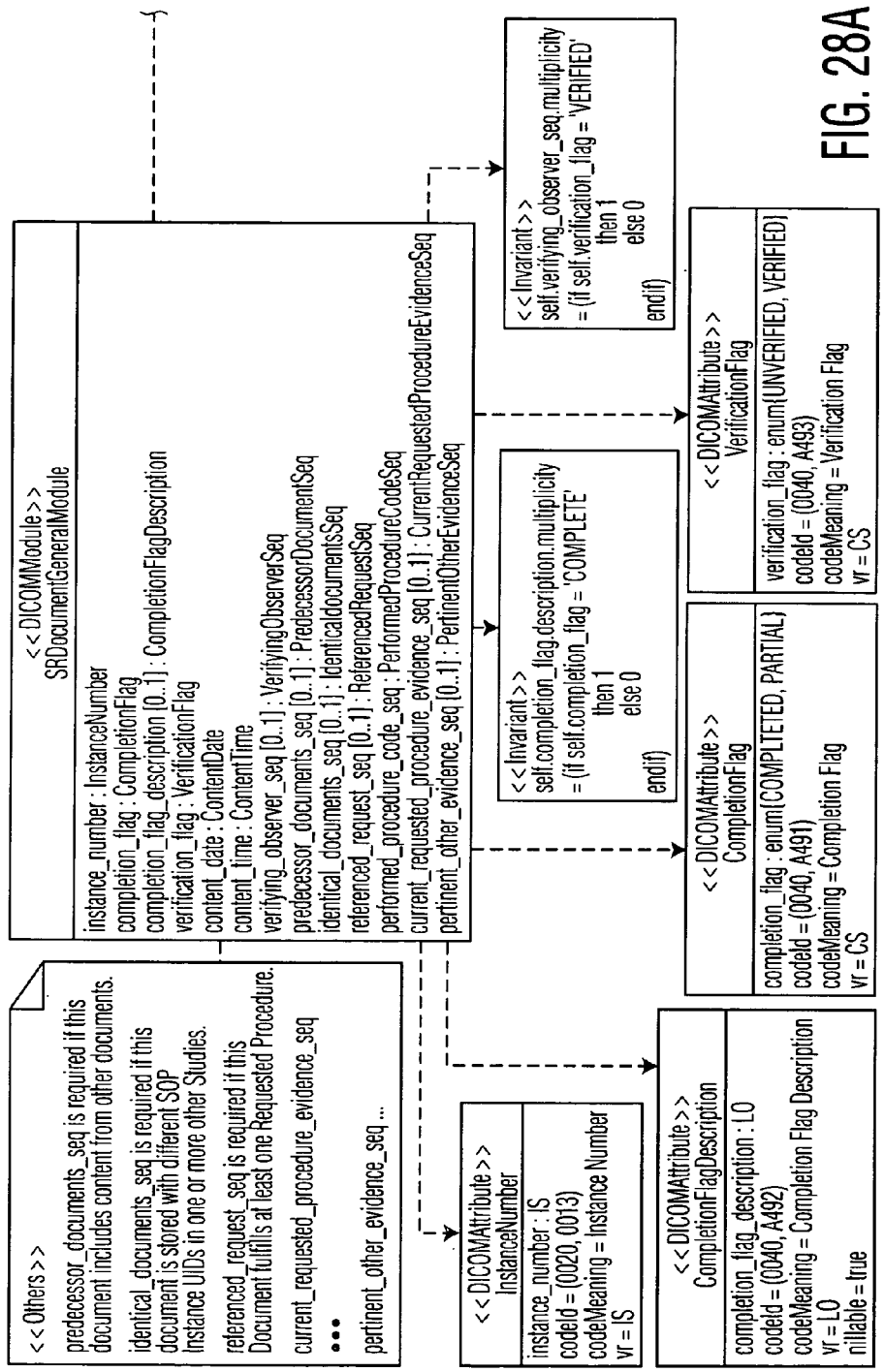
Figure 28B:
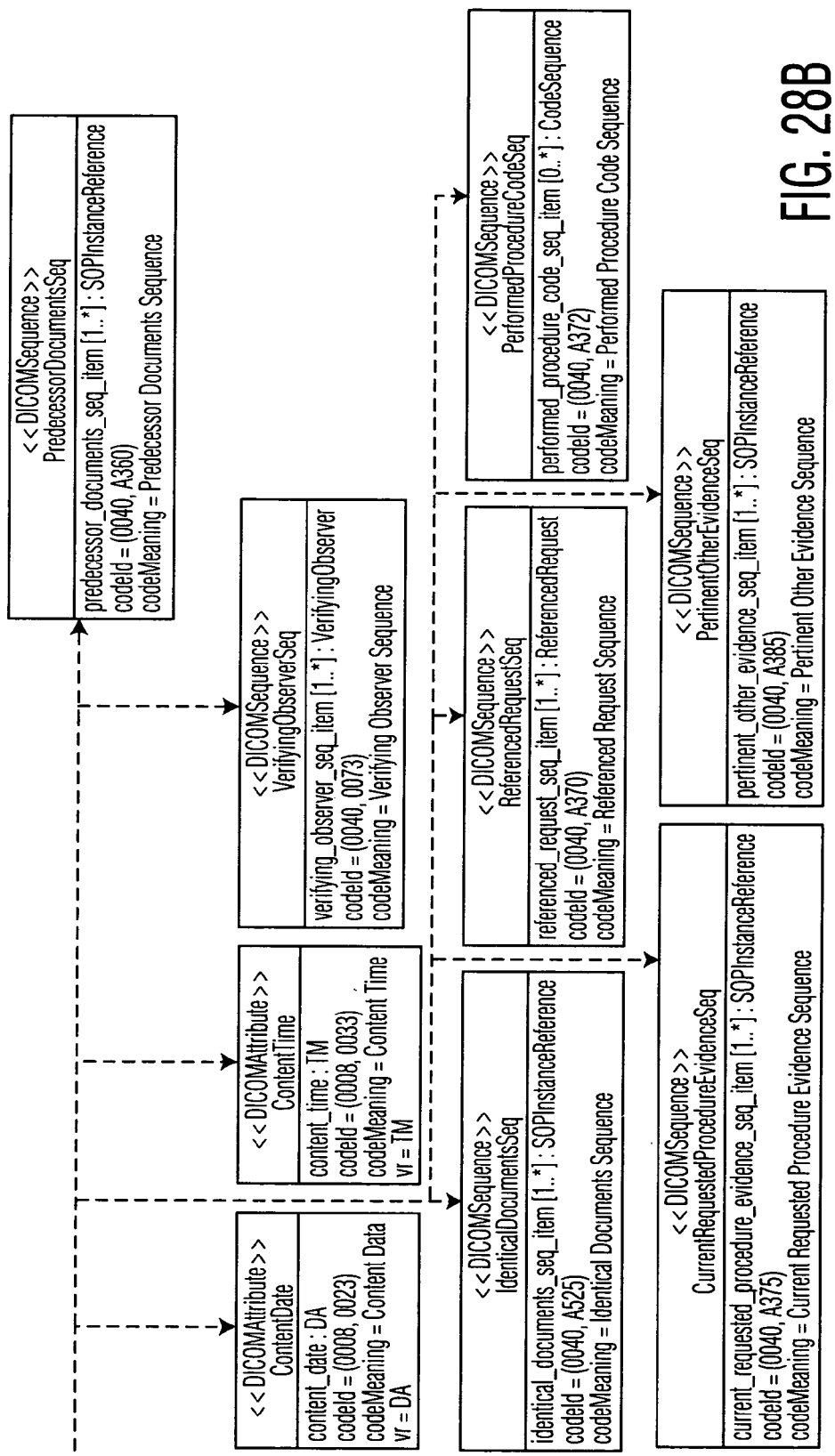
Figure 29:
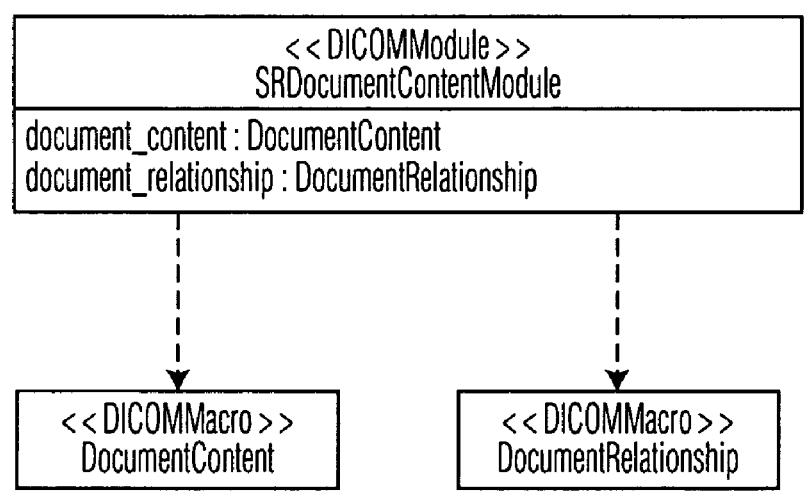
Figure 30:
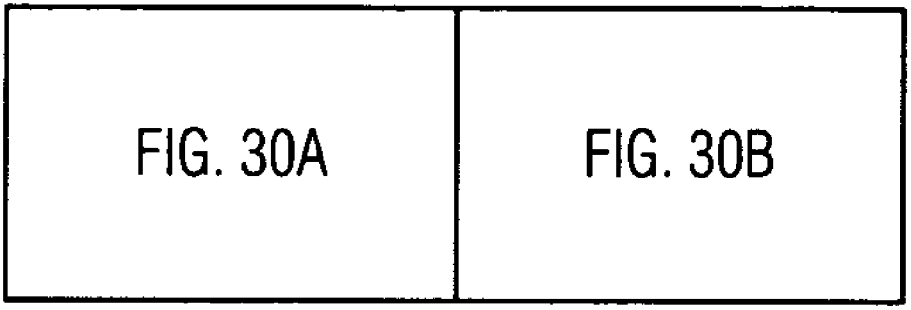
Figure 30A:
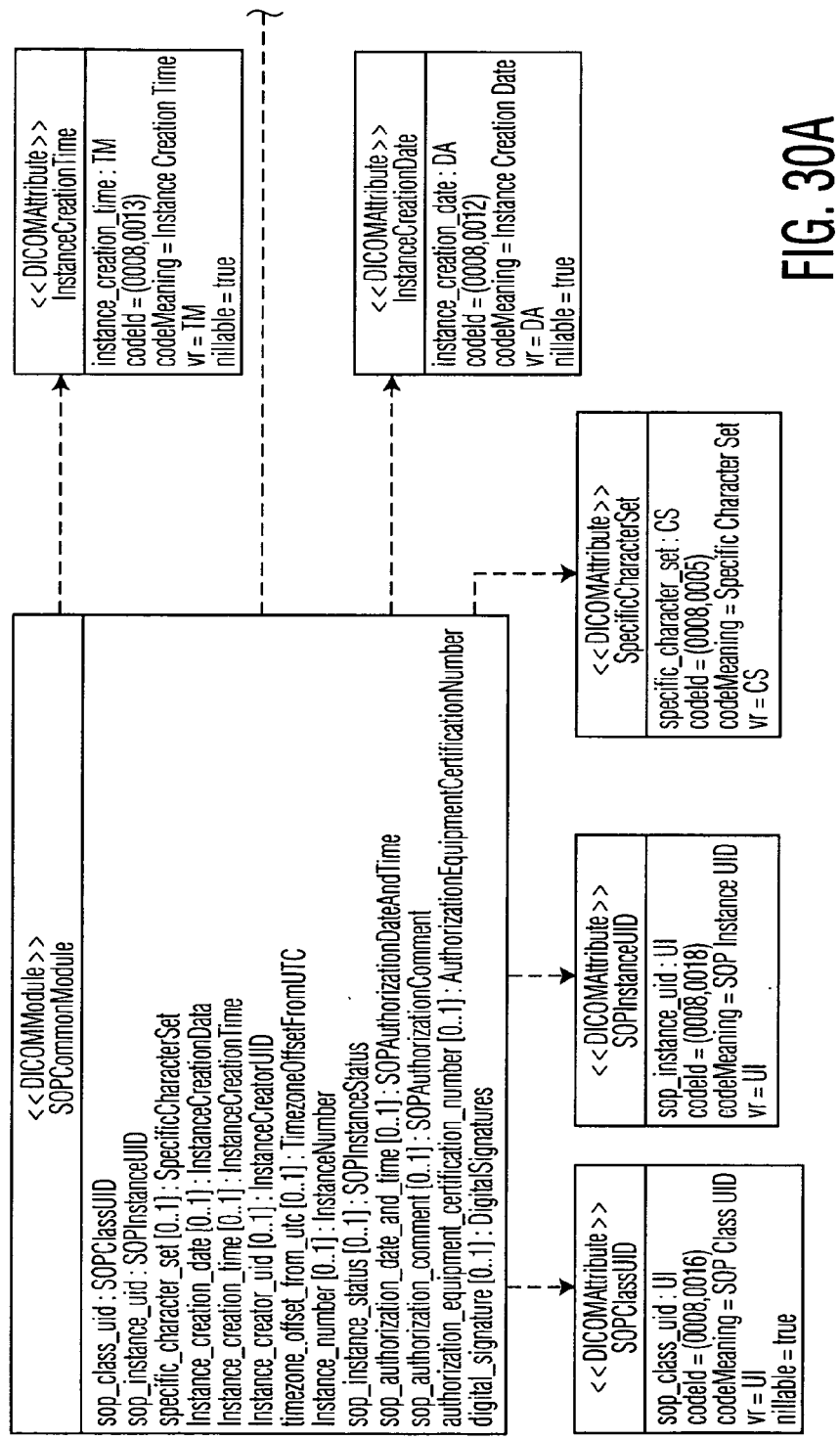
Figure 30B:
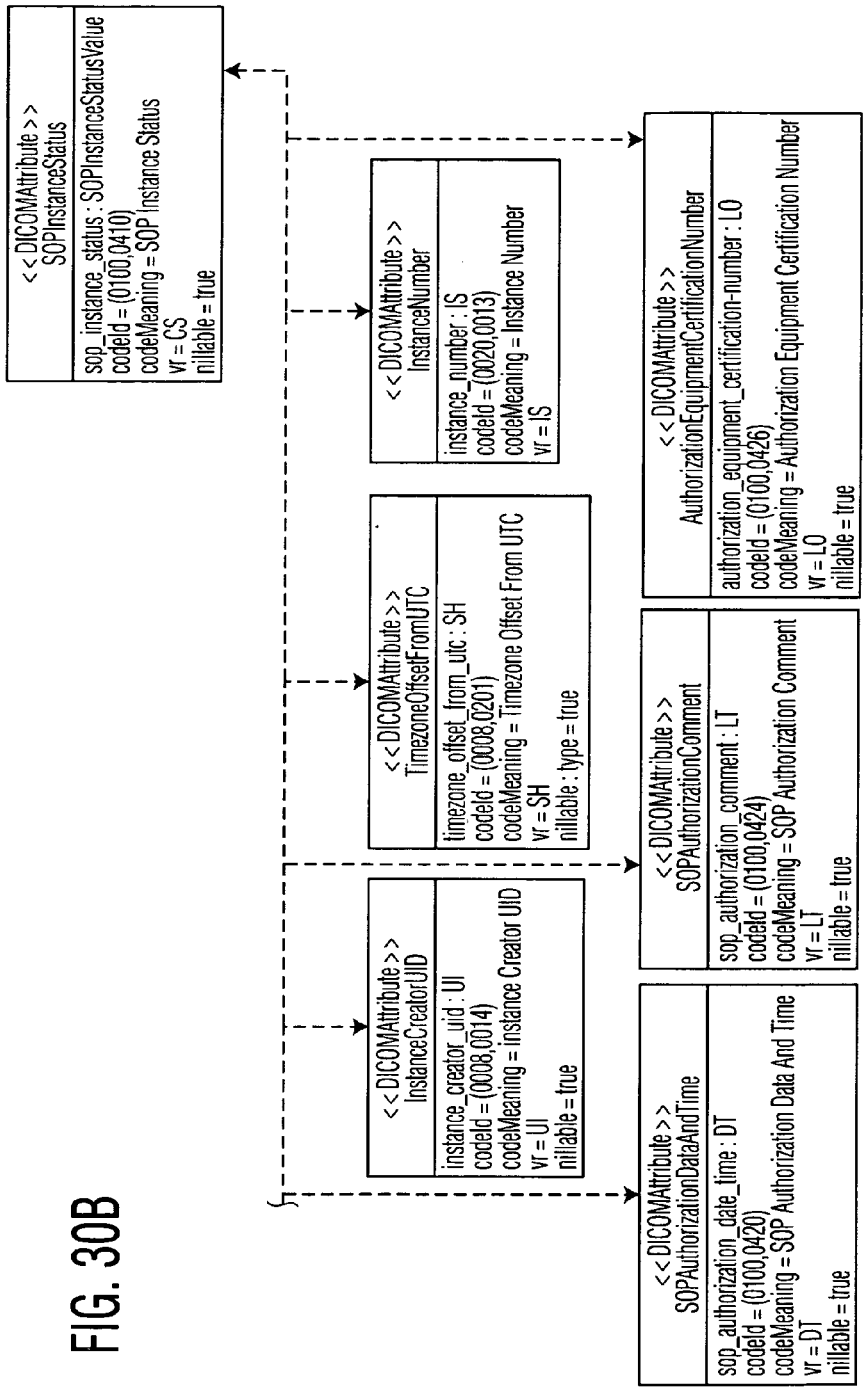
Figure 31:
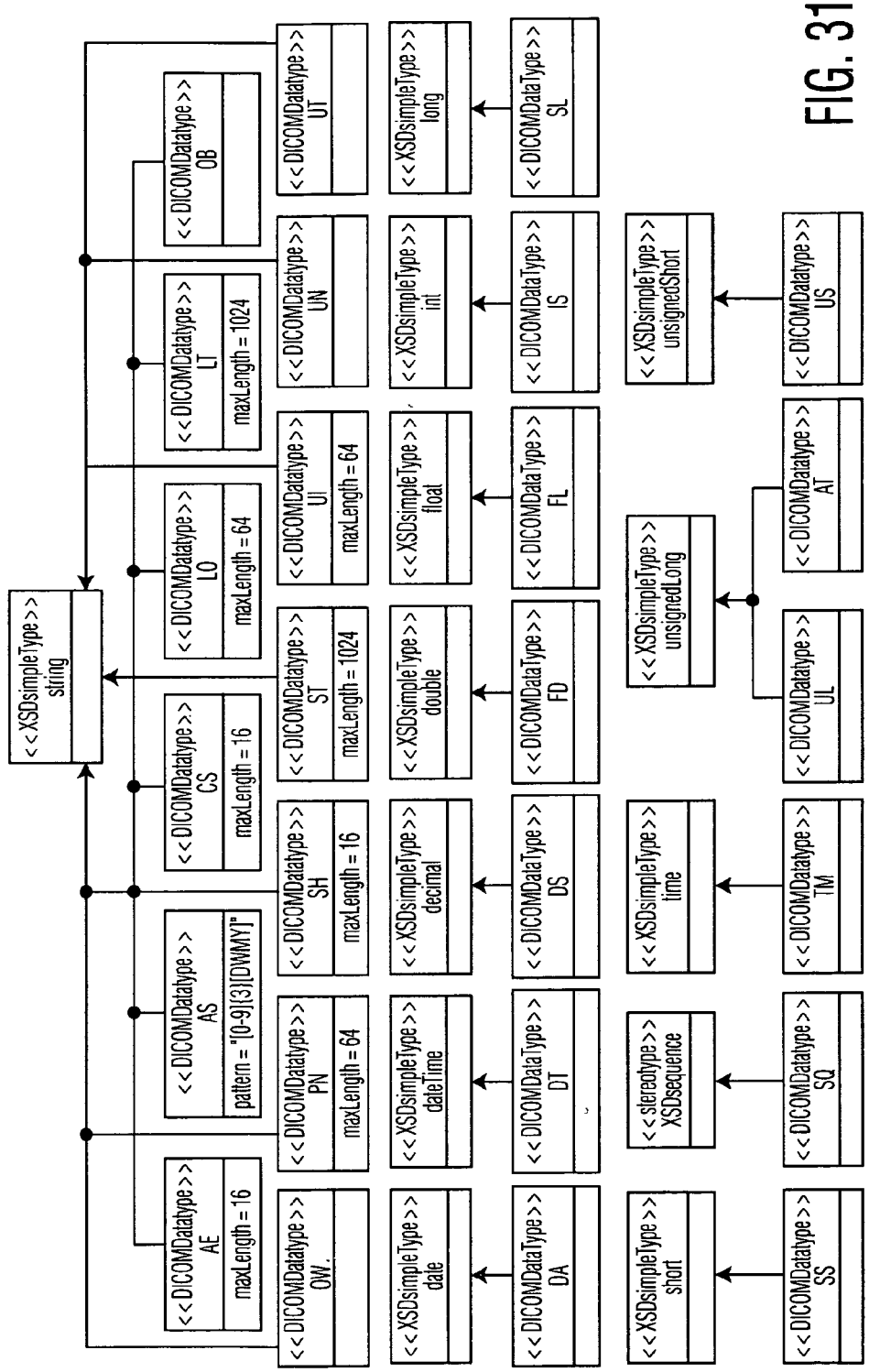
Figure 32:
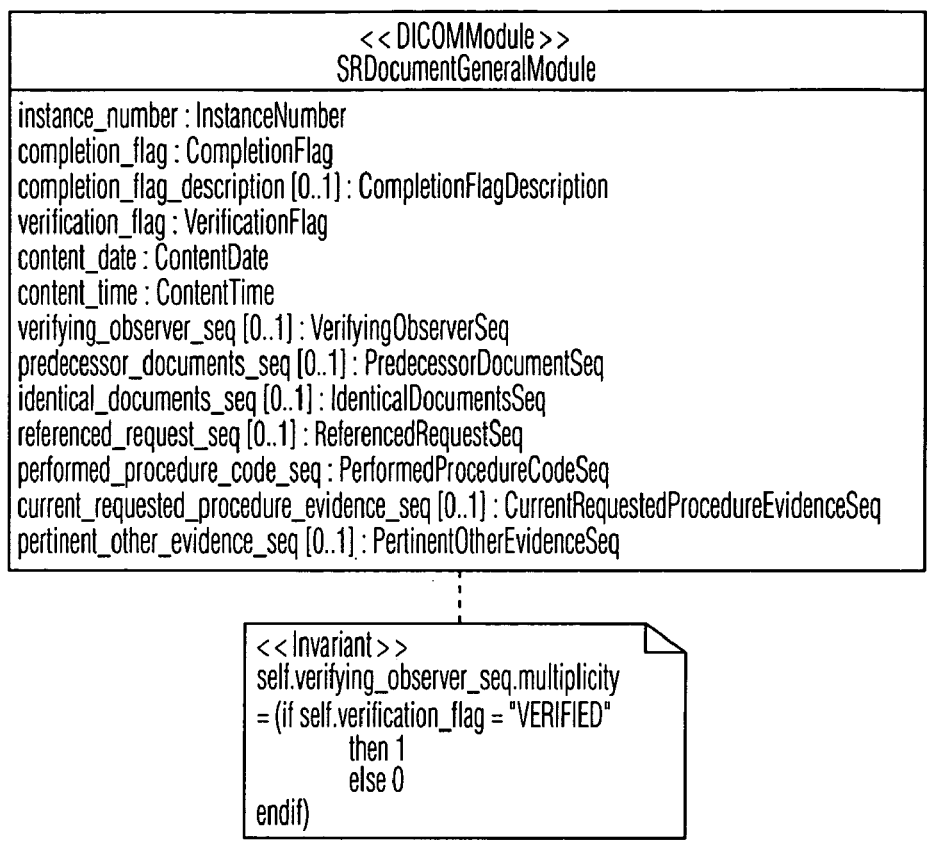
Figure 33:
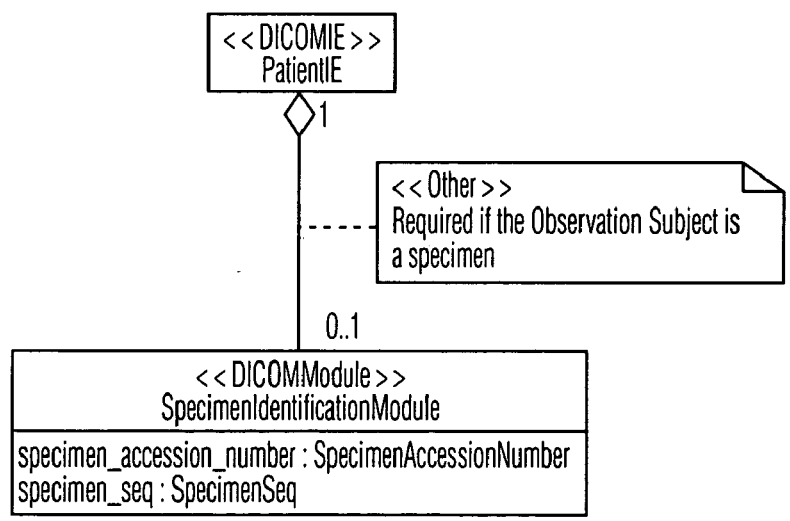

FIG. 6 a diagram which sets forth the stereotype definitions derived from the UML profile for DICOM information model;

FIG. 7 is a diagram which shows a sample of constraints on Associations (Prior Art);

FIG. 8 is a diagram which shows a UML package of DICOM IODs;

FIG. 9 is a diagram which shows a UML package diagram of the DICOM information model or template taught hereby;

FIG. 10 is a diagram which shows the High-level structure of SR Comprehensive DICOM IOD;

FIG. 11 is a diagram which shows a UML class of Patient Module in accordance with the UML profile for DICOM information model;

FIG. 12 is a diagram which shows a Numeric Measurement Macro class diagram in accordance with the present invention;

FIG. 13 is a diagram which shows a Referenced Patient Sequence class diagram in accordance with the represent invention;

FIG. 14 is a diagram which shows a Measured Value Sequence class diagram in accordance with the present invention;

FIG. 15 is a diagram which shows a Class diagram of DICOM Patient's Name Attribute provided in accordance with this invention;

FIG. 16 is a diagram which shows a portion of a UML diagram of Document Content Macro with constraints, in accordance with this invention;

FIG. 17 is a diagram which shows an Invariant representation for DateTime DICOM Attributes in accordance with this invention;

FIG. 18 is a diagram which shows a UML model of SOP Common Module in accordance with this invention;

FIG. 19 is a diagram which shows a UML model of selected DICOM data types in accordance with this invention;

FIG. 20 is a diagram which shows an enumeration representation of a DICOM Continuity Of Content Attribute in accordance with this invention;

FIG. 21 is a diagram which shows an enumeration stereotype of DICOM Value Type Attribute in accordance with this invention;

FIG. 22 is a diagram which shows a Patient Module in accordance with this invention;

FIG. 23 is a diagram which shows a Specimen Identification Module in accordance with this invention;

FIG. 24 is a diagram which shows a General Study Module in accordance with this invention;

FIG. 25 is a diagram which shows a Patient Study Module in accordance with this invention;

FIG. 26 is a diagram which shows an Document Series Module in accordance with this invention;

FIG. 27 is a diagram which shows a General Equipment Module in accordance with this invention;

FIG. 28 is a diagram which shows an DICOM Document General Module in accordance with this invention;

FIG. 29 is a diagram which shows an DICOM Document Content Module in accordance with this invention;

FIG. 30 is a diagram which shows an SOP Common Module in accordance with this invention;

FIG. 31 a diagram which depicts DICOM Value Representations in accordance with this invention;

FIG. 32 is a diagram showing an invariant constraint of verifying_observer_seq in accordance with this invention; and FIG. 33 is a diagram which shows a sample of unexpressed constraint in accordance with this invention.

DETAILED DESCRIPTION OF THE INVENTION

The Unified Modeling Language (UML), standardized by the Object Management Group (OMG), provides an industry standard modeling language for modeling object-oriented programs. Representing the DICOM information model in UML, as set forth and claimed herein, will make the DICOM information model in UML more clear and improve DICOM communication among information architects and software developers. Using UML tools, source code may be generated for common programming languages such as Java and C++. The prior art includes commonly owned and copending application Ser. No. 09/686,401, which discloses an invention which uses the Extensible Markup Language (XML) from OMG such that DICOM XML Document Type Definitions (DTDs) may be generated from UML models, as well as UML modeling of XML representation of DICOM, incorporated herein by reference. XML is a meta language which allows a user to define a proprietary markup to describe the structure of data, for example, a database for exchange of medical information between two entities linked by the world wide web.

Information Model

Figure 1:
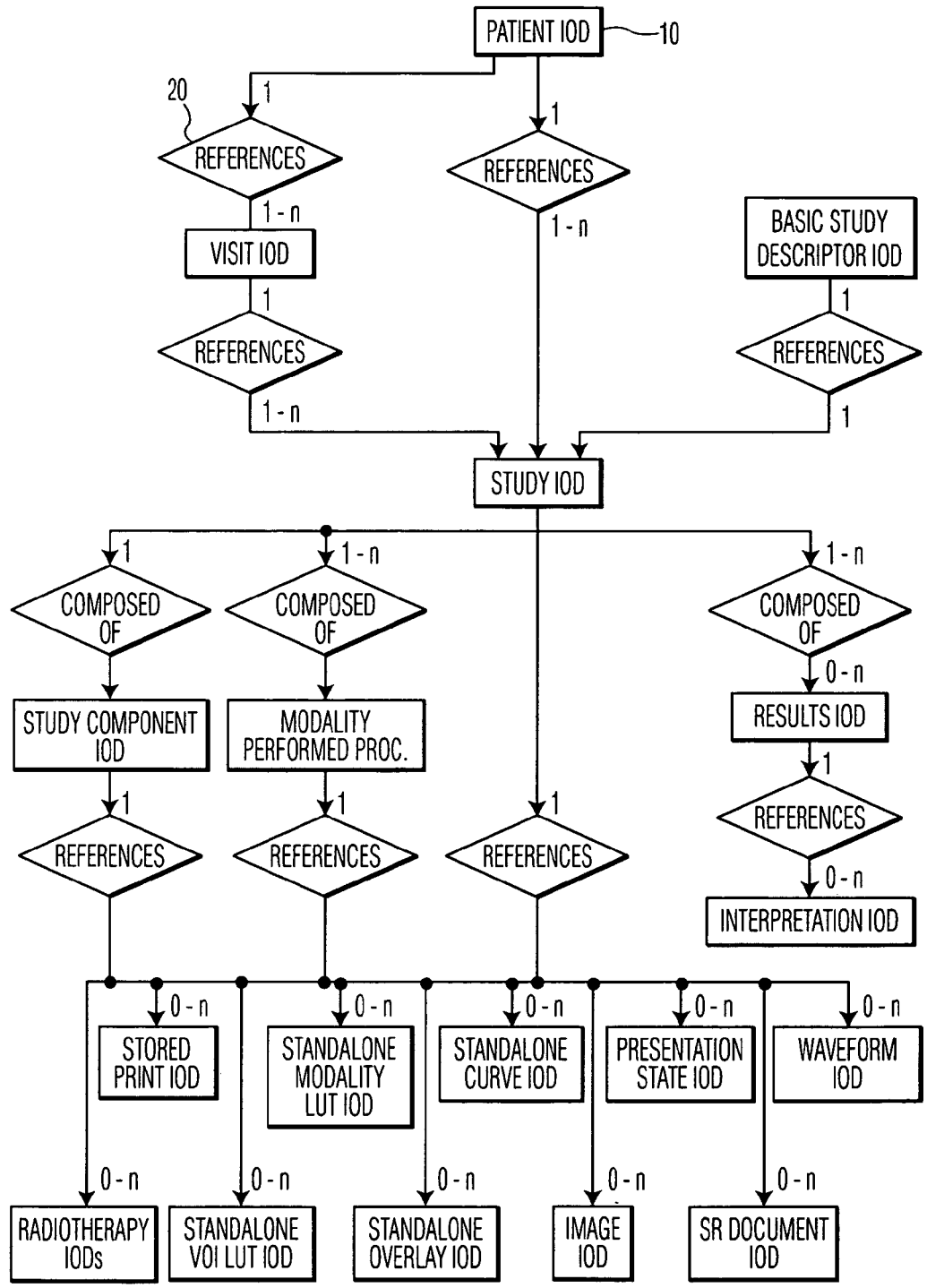
FIG. 1 is a diagram which broadly depicts the DICOM Information model (PRIOR ART)

The DICOM information model relies on explicit and detailed models of how the "things" (patients, images, reports, etc) involved in medical imaging operations are described, and how they are related. These models are called E-R models and are a way to be sure that manufacturers and users understand the basis for developing the data structures used in DICOM (FIG. 1). That is, FIG. 1 shows rectangular boxes 10, which may represent entities which singly or in combination, form the information objects. The diamond-shaped boxes 20 represent relationships, the arrows represent the connections between entities and relationships. Each IOD consists of a set of information entities (IEs), containing one or more modules, as seen in Table 1.

TABLE 1

Comprehensive DICOM IOD definition

| IE | Module | Usage |
| --- | --- | --- |
| Patient | Patient | M |
|  | Specimen | C - Required if the Observation Subject is a Specimen |
| Study | General Study | M |
|  | Patient Study | U |
| Series | SR Document Series | M |
| Equipmen | General Equipment | M |
| Document | SR Document General | M |
|  | SR Document Content | M |
|  | SOP Common | M |

Usage indicates if such a Module is M—mandatory, C—conditional, or U—user optional. Each Module has a set of Attributes which may be atomic Attributes, Macros, or Sequence Attributes, as seen in Table 2.

TABLE 2

General Study Module

| Attribute Name | Tag | Type | Attribute Description |
| --- | --- | --- | --- |
| Study Instance UID | (0020,000D) | 1 | Unique identifier for the Study. |

TABLE 2-continued

General Study Module

| Attribute Name | Tag | Type | Attribute Description |
|---|---|---|---|
| Study Date | (0008,0020) | 2 | Date the Study started. |
| Study Description | (0008,1030) | 3 | Institution-generated description or classification of the Study (component) performed. |
| Referenced Study Sequence | (0008,1110) | 3 | A sequence which provides reference to a Study SOP Class/ Instance pair. The sequence may have zero or more Items. |
| >Referenced SOP Class Sequence | (0008,1150) | 1C | UID Uniquely identifies the referenced SOP Class. Required if Referenced Study (0008,1110) is sent. |
| >Referenced SOP Instance UID | (0008,1155) | 1C | Uniquely identifies the referenced SOP Instance. Required if Referenced Study Sequence (0008,1110) is sent. |
| Procedure Code Sequence | (0008,1032) | 3 | A Sequence that conveys the type of procedure performed. One or more Items may be included in in this Sequence. |

Table 2 should make clear that an atomic Attribute such as Study Instance UID does not contain any other Attributes. A Sequence Attribute, e.g., Referenced Study Sequence contains two atomic Attributes. Sometimes, a Sequence Attribute may contain other Sequence Attributes or Macros, e.g., Procedure Code Sequence contains Code Sequence Macro, not shown in this document. A Macro has the same structure as a Module. The Tag gives the DICOM Tag for a specific DICOM Attribute. The Type specifies if an Attribute is mandatory or optional with constraints. An Attribute is required and the length of its value field shall not be zero if it is Type 1. Type 1C has the same requirements as Type 1 under some conditions. An Attribute is required and the length of its value field may or may not be zero if it is Type 2. Type 2C has the same requirements as Type 2 under some conditions. Type 3 is optional and can be zero length or no value.

Within or among Modules or Macros, there may exist some constraints, e.g., Document Content Macro (see Table 3).

TABLE 3

Part of Document Content Macro

| Attribute Name | Tag | Type | Attribute Description |
|---|---|---|---|
| Value Type | (0040,A040) | 1 | The type of the value encoded in this Content Item. Defined Terms: TEXT, NUM, CODE, DATE-TIME, DATE, TIME, UIDREF, PNAME, COMPOSITE, IMAGE, WAVEFORM, SCOORD, TCOORD CONTAINER |
| Continuity of Content | (0040,A050) | 1C | This flag specifies for a CONTAINER whether or not its contained Content Items are logically linked in a continuous textual flow, or are separate items. Required if Value Type |

TABLE 3-continued

Part of Document Content Macro

| Attribute Name | Tag | Type | Attribute Description |
|---|---|---|---|
| | | | (0040,A040) is CONTAINER. Enumerated Values: SEPARATE CONTINUOUS See C.17.3.2 for further explanation. |
| DateTime | (0040,A120) | 1C | This is the value of the Content Item. Required if Value Type (0040,A040) is DATETIME. |
| Date | (0040,A121) | 1C | This is the value of the Content Item. Required if Value Type (0040,A040) is DATE. |

As shown above, Value Type, a Type 1 Attribute, has defined terms such as DATE, DATATIME, and NUM. And Date Attributes, a Type 1C, is required only if Value Type is DATE. specifies the data structures and Value Representations (VRs). Table 4 lists some of the VRs.

TABLE 4

Definition of VRs

| VR Name | Definition | Character | Repertoire | Length |
|---|---|---|---|---|
| AE Application Entity | A string of characters with leading and trailing spaces (20H) being non-significant. The value made of 16 spaces, meaning "no application name specified", shall not be used. | | Default Character Repertoire excluding control characters LF, FF, CR and ESC. | 16 bytes maximum |
| AS Age String | A string of characters with one of the following formats -- nnnD, nnnW, nnnM, nnnY; where nnn shall contain the number of days for D, weeks for W, months for M, or years for Y. Example: "018M" would represent an age of 18 months. | | "0"–"9", "D", "W", "M", "Y" of Default Character Repertoire | 4 bytes fixed |
| CS Code String | A string of characters with leading or trailing spaces (20H) being non-significant. | | Uppercase characters, "0"–"9", the SPACE character, and underscore "_", of the Default Character Repertoire | 16 bytes maximum |

Each VR specifies its value pattern or restricts the length of the value field, e.g., AS—Age String, is a value of three digits followed by "D", "W", "M", or "Y". There are 26 VRs defined in the version of DICOM2001 specification. As shown above, the DICOM IODs are not represented in a standard modeling language and are not machine-readable, which forms a barrier to the communication between DICOM and non-DICOM information architects and developers. Therefore, a standard modeling representation of The DICOM information model is needed for common communication. UML, an industry modeling standard, is such a language. In order to represent such finer information over UML class diagrams clearly, a UML profile for DICOM is needed. The UML modeling of representing DICOM constraints, DICOM Attribute information including DICOM Tags, Types, and Enumerated values is called precise UML modeling.

UML Profile for Dicom Information Model

A UML profile is a stereotyped package that contains model elements that have been customized for a specific domain or purpose by extending the meta-model using UML extension mechanisms including stereotypes, tagged definitions, and constraints. The inventive UML profile for DICOM provides a set of model elements customized specifically for DICOM using extension. It serves as a set of class model templates to help build UML models for DICOM IODs. As discussed above, DICOM specifies a set of IOs such as IODs, IEs, Modules, Macros, and Attributes. The UML profile for DICOM provides an ability to build UML models for DICOM IODs where an associated UML stereotype with each DICOM IO and DICOM data type. Such a UML stereotype may have tagged values if it is defined for DICOM Attributes, where the tagged values specify the DICOM Attribute name, DICOM Tag, and DICOM Type. The inventive UML profile for DICOM may also have constraints, e.g., DICOM IOD which is always a top-level class. Each stereotype is named based on DICOM terms, not UML terms. These new and unique stereotypes, tagged values, and constraints together constitute the inventive UML profile for DICOM. The inventive UML profile for DICOM provides for guidance for the generation of UML models for The DICOM information model.

Figure 2A:
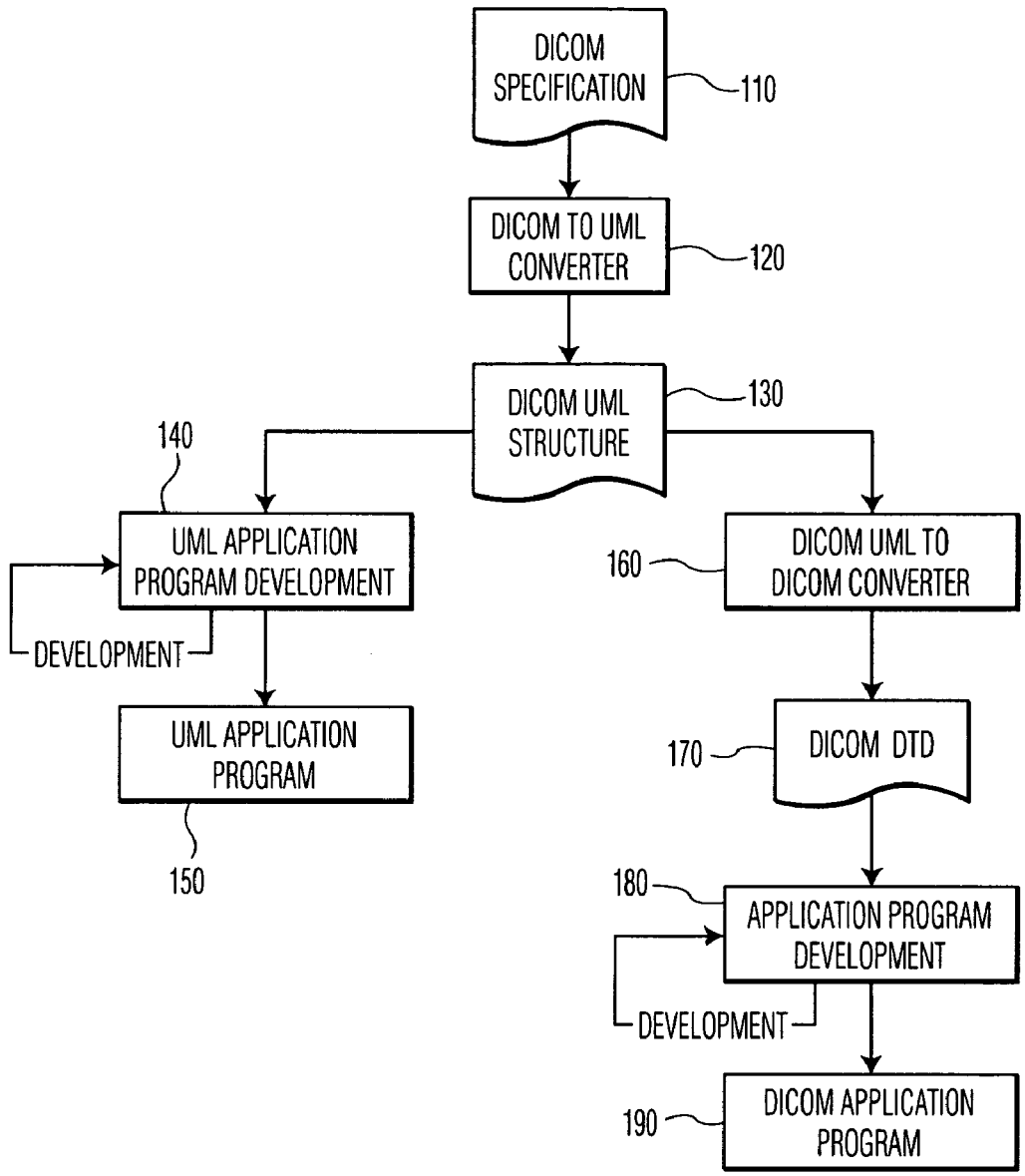
FIG. 2A is a schematic flow diagram which illustrates conversion of the DICOM specification into UML which facilitates program development in accordance with this invention.

FIG. 2A illustrates an example flow diagram for converting the DICOM specification 110 into UML 130 and DICOM DTD170 representations that facilitate program development in accordance with this invention. As noted above, although applications can be developed that utilize DICOM's relational structured reporting scheme directly, it can be expected that the number of programmers and other computer professions who are familiar with UML and object-oriented technologies and techniques will be substantially greater than those who are familiar with DICOM and relational technologies and techniques.

This invention is also based on the premise that DICOM-related application programs can be more efficiently developed as UML enabled applications. This efficiency is gained by presenting the DICOM structure in the context of a UML structure, i.e., the model or template, thereby eliminating the learning curve and context-switch difficulties typically encountered when dealing with new languages. As is known in the art, the assimilation of the rules, conventions, idiosyncrasies, etc. of a language generally comes with time and experience. In like manner, the appreciation of the interrelationships among data items and entities is highly dependent upon an appreciation of the interactions and dependencies that are implied by the modeling language used to express these interrelationships. By presenting the DICOM specification as a UML representation, the experiences of the UML programmer, systems analyst, technical writer, engineer, manager, etc. are advantageously used, thereby potentially reducing the costs associated with an application program development.

As illustrated in FIG. 2A, a converter 120 converts the elements of the DICOM specification 110 into elements of a UML structure 130. This UML structure 130 can be used to facilitate the development 140 of an application program 150 that uses the UML structure 130, or it can be further converted, via converter 160, into elements of an DICOM Document Type Definition (DTD), illustrated at 170. The DICOM DTD 170 facilitates the development 180 of an DICOM-enabled application program 190.

Note that the UML application program development 140 and the DICOM application program development 180 can be expected to require fewer resources than an application program development that uses the DICOM specification directly. A number of UML utility routines can be expected to be available for use in this development, based on the increasing use of UML in the computer industry. Also, UML is an object-oriented language, and an objective of the object-oriented paradigm is to facilitate the transport and re-use of object-oriented software.

Figure 2B:
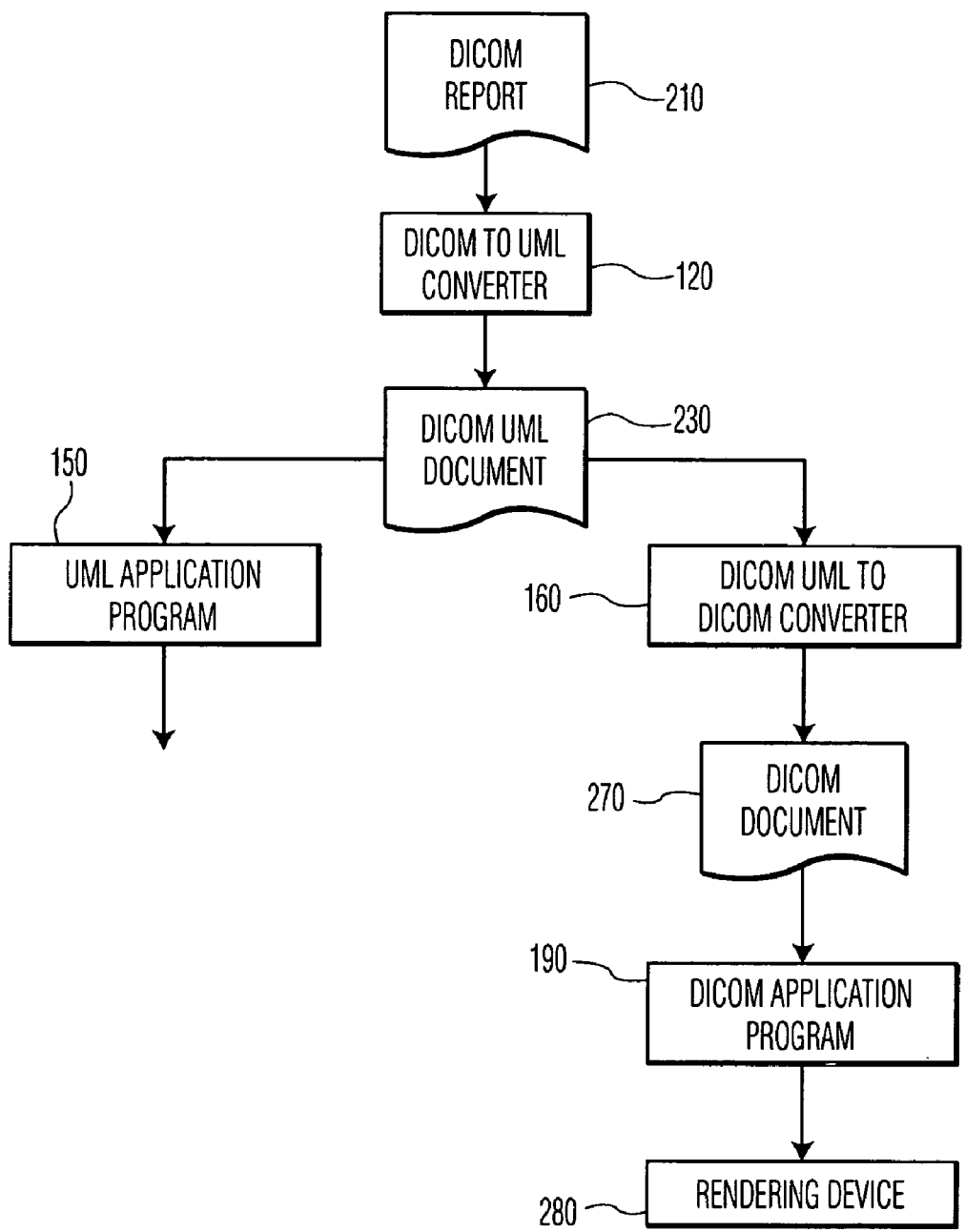
FIG. 2B is a schematic flow diagram which illustrates conversion of the DICOM reports into UML for processing by UML enabled applications in accordance with this invention.

FIG. 2B illustrates an example flow diagram for converting the DICOM reports 210 into UML 230 and DICOM 270 documents for processing by the aforementioned UML 150 and DICOM 190 enabled applications, in accordance with this invention. That is, the programs 150, 190 whose development was facilitated by the DICOM converters 120, 160 of this invention, or other UML programs, can be used to process individual DICOM reports 210, merely by converting the reports 210 into corresponding UML 230 and DICOM 270 documents, respectively. Note that the term "document" is used herein for ease of reference, and includes any of a variety of embodiments, including data that is temporarily or permanently stored in a file, data that is stored in memory, or on a disk, data that is communicated among processing systems, and so on. The UML 150 or DICOM 190 applications may include, for example, applications that render 280 the content of the individual DICOM report 210 for viewing by a diagnostician, applications that transfer the content of the individual DICOM report 210 to processing facilities that do not have DICOM enabled applications, applications that collect the information from individual DICOM reports 210 and perform analyses for clinical studies, and so on.

Figure 3:
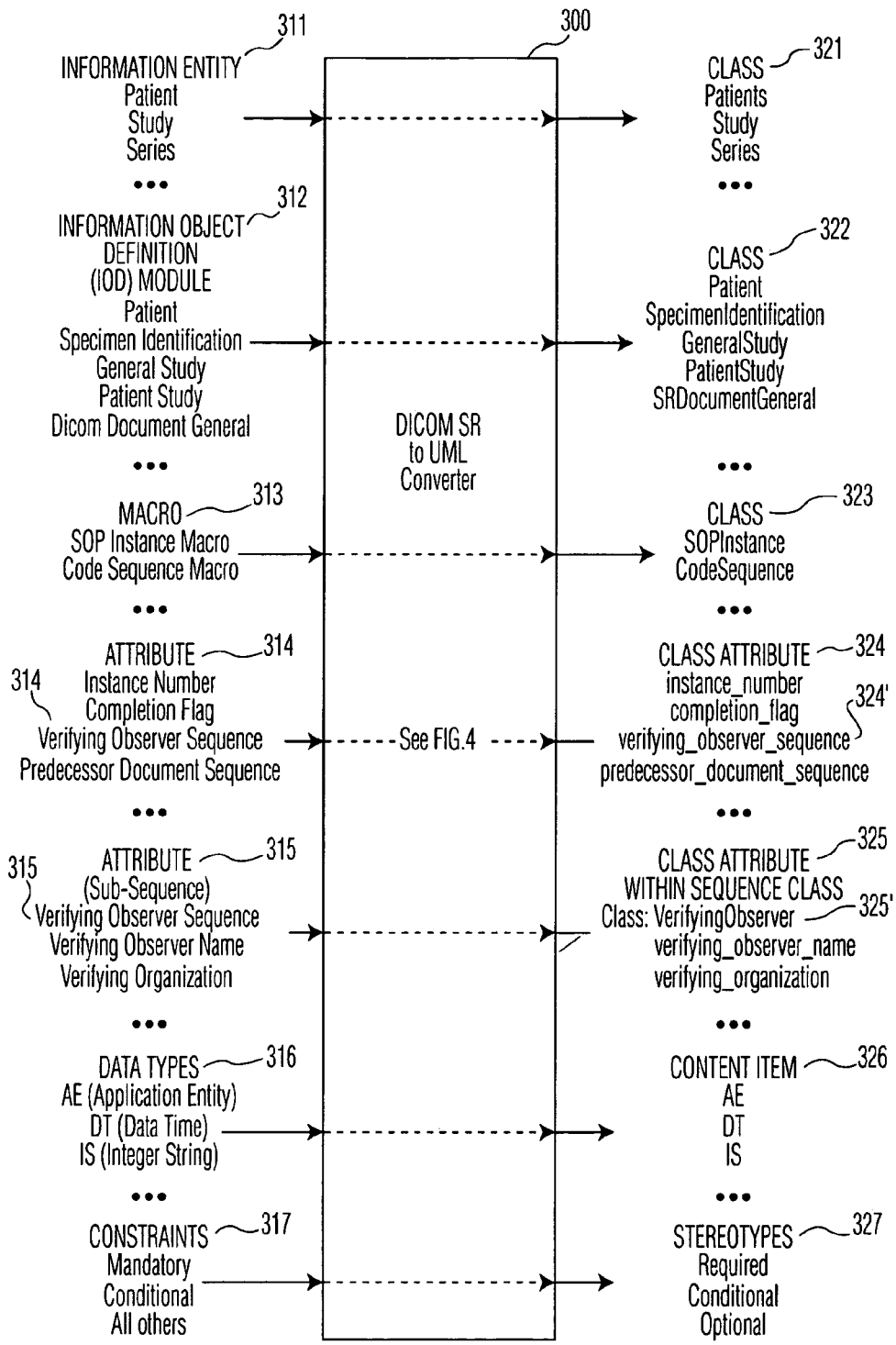
FIG. 3 is a diagram which illustrates an embodiment of the DICOM to UML converter in accordance with this invention.

FIG. 3 illustrates an example DICOM to UML converter 300. Example DICOM entities 311-317 are illustrated on the left of the converter 300, and corresponding UML entities 321-327 are illustrated on the right of the converter 300. In accordance with this invention, particular rules are associated with the various DICOM entity types to effect the conversion. FIG. 3 is provided for exemplary purposes, and is by no means exhaustive, as will be readily seen by those skilled in the art.

Figure 4A:
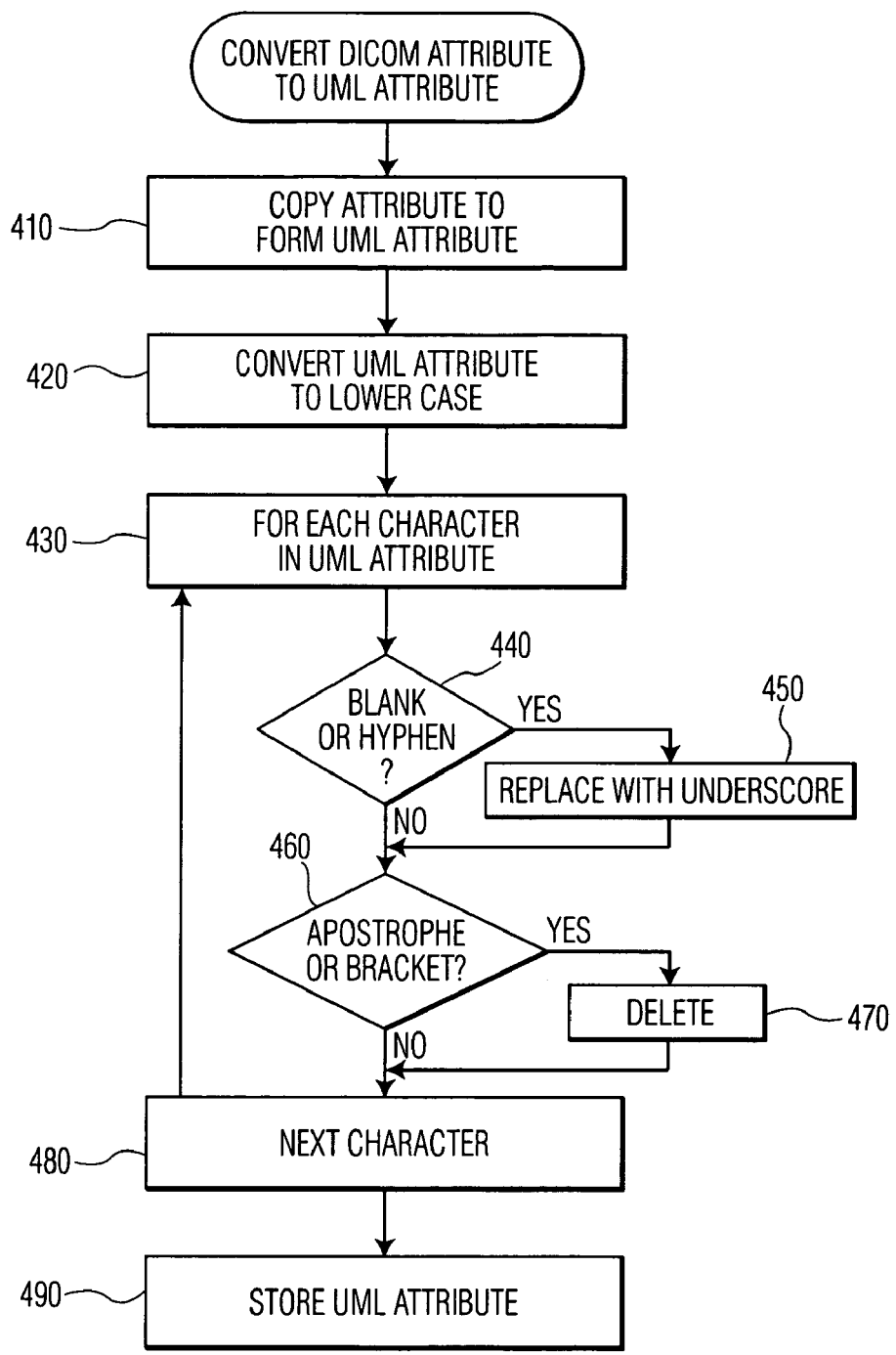
FIG. 4A is a schematic flow diagram which illustrates conversion of a DICOM attribute into a UML attribute in accordance with this invention.

FIG. 4A illustrates an example flow diagram for converting DICOM Attribute names to UML Class Attribute names. The DICOM attribute name is initially copied to form the UML attribute name, at 410, and converted to lower case, at 420. Via the loop 430-480, each blank and hyphen character is identified, at 440, and replaced with an underscore character, at 450, and each apostrophe or bracket character is identified, at 460, and deleted from the UML attribute name, at 470. The resultant UML attribute name is stored, at 490.

Figure 4B:
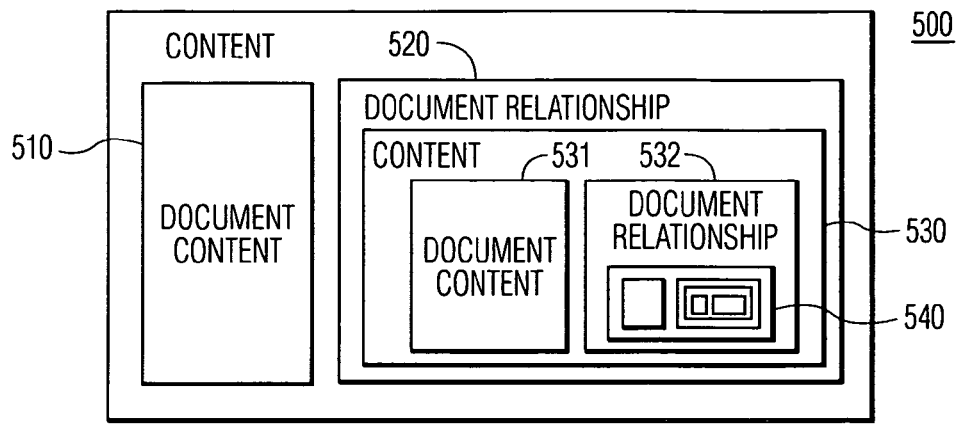
FIG. 4B is a schematic flow diagram which illustrates conversion of the DICOM recursive data element into a set of UML elements in accordance with this invention.
Figure 4C:
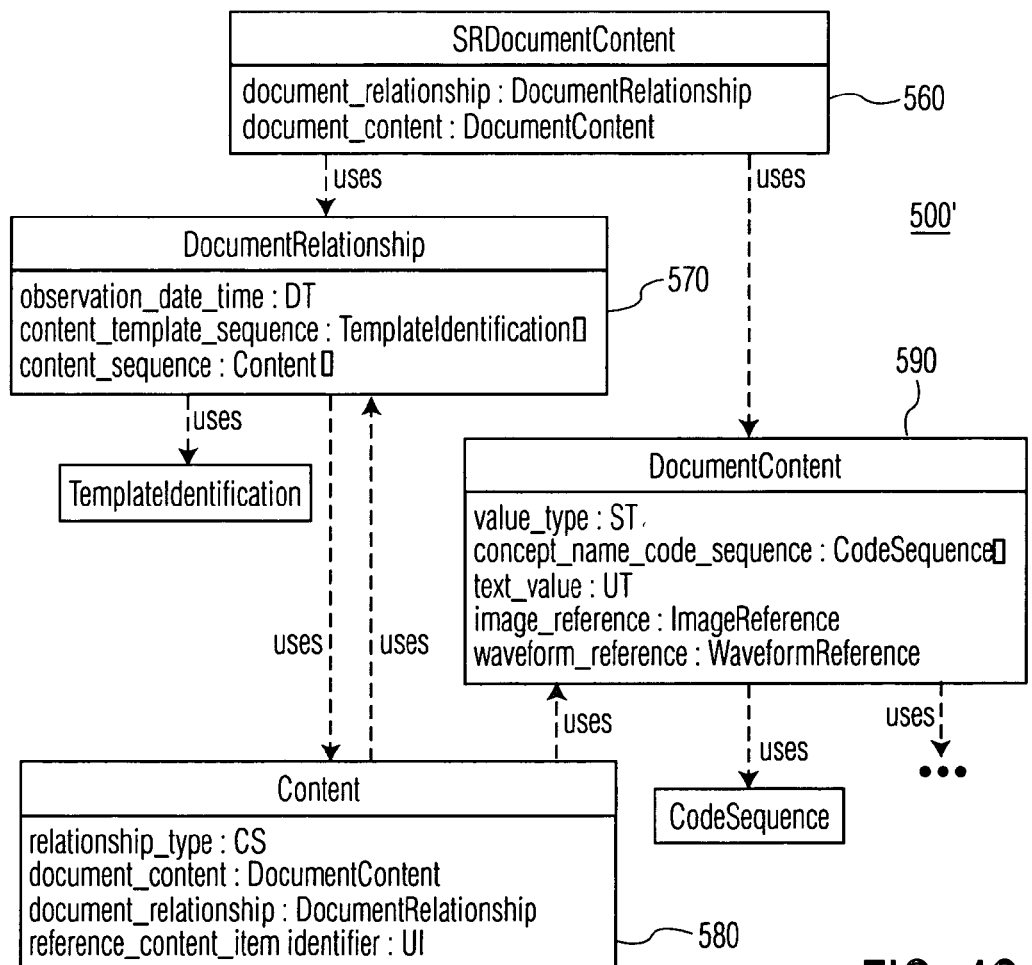
FIG. 4C is a diagram which illustrates a UML representation of a DICOM information object Definition (IOD) Module in accordance with this invention.

The DICOM enables Content Items unlimited recursion. FIG. 4B illustrates this recursion in the DICOM Document Content module 500, via the Document Relationship Macro 520. As illustrated, the Document Relationship Macro 520 may include a Content module 530, and this Content module 530 may contain a document relationship 532 that includes another Content module 540, and so on. In accordance with this invention, as illustrated in FIG. 4C, the DICOM Document Content UML representation 560 includes elements DocumentRelationship 570 and DocumentContent 590, and the Document Relationship representation 570 and the Content representation 580 each reference each other, thereby effecting a recursive relationship.

Using the above rules for mapping the elements of DICOM into corresponding elements of UML, DICOM specification documents and DICOM content documents are converted into a modeling language that is more often used by computer professionals, thereby providing the opportunity to ease the task and cost of producing application programs that can be used for processing DICOM related material.

Figure 5:
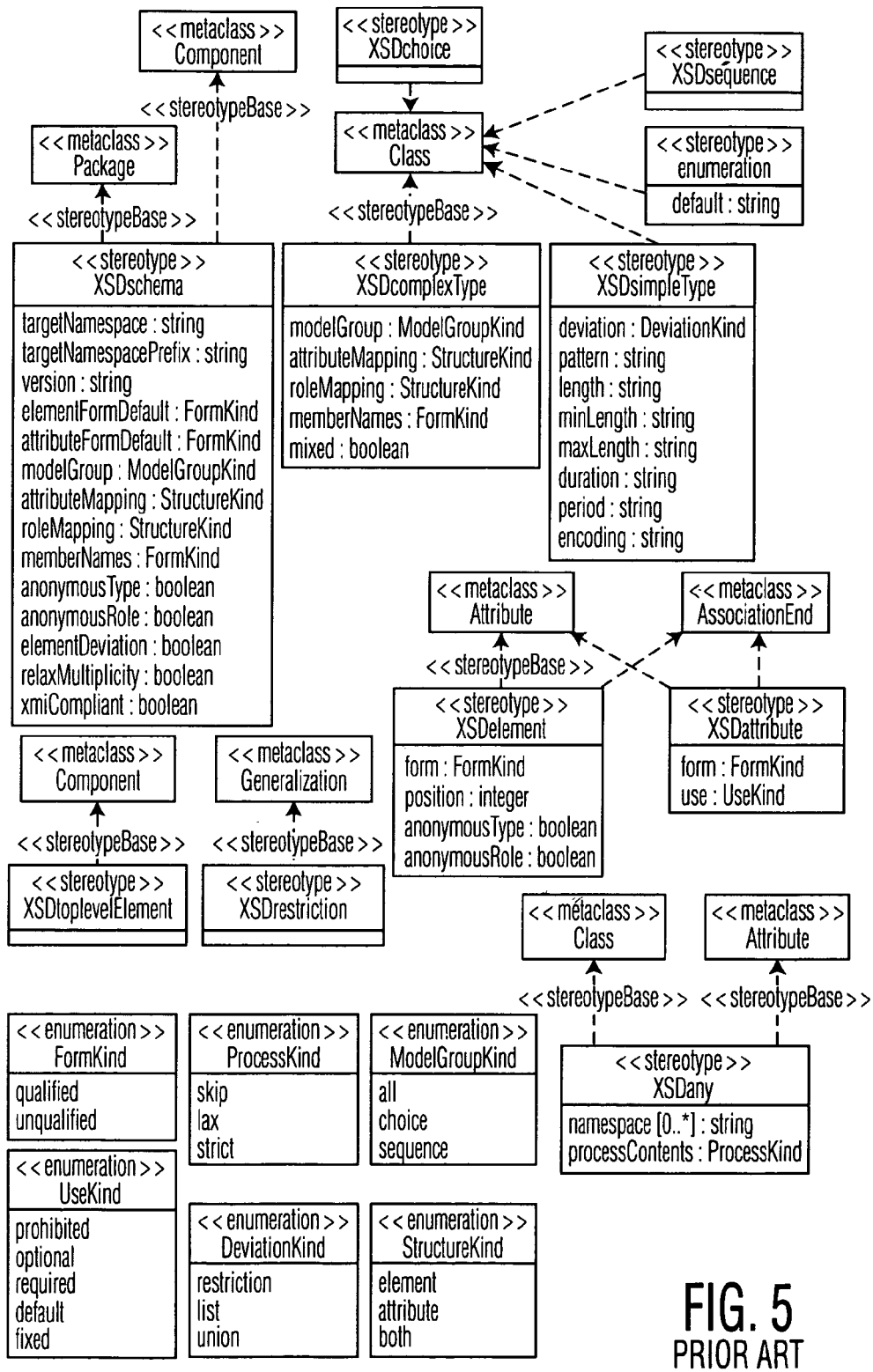
FIG. 5 is a diagram which sets forth the stereotype definitions derived from the UML profile for XML Schema (Prior Art)

FIG. 5 is a description of prior art UML profile for XML schema. XML applications in UML are discussed by Carlson, David, MODELING XML APPLICATIONS WITH UML-PRACTICAL E-BUSINESS APPLICATIONS, Addison-Wesley, 2001.

As discussed above, the DICOM information model contains a set of IODs, IEs, Modules, Macros, Sequences, and atomic Attributes. In order to guide the generation of UML models for each IOD, a stereotype is defined for each IO. The inventive UML profile for DICOM is shown in FIG. 6. Those skilled in the art will understand that the FIG. 6 description is not exhaustive, and may be extended with new stereotypes if necessary. Each of the FIG. 6 stereotypes is also described in Table 5.

TABLE 5

Summary of stereotype description of DICOM profile

| Stereotype | Base Class | Description | Tagged values | Constraints |
|---|---|---|---|---|
| IOD | XSDtopLevelElement | A IOD stereotype represents a DICOM IOD definition containing a set of DICOM IEs. It can be represented as a top level element in XML Schema representation. | None. | This class must be assigned to exactly one class. |
| IE | XSDcomplexType | A IE stereotype represents a DICOM IE which contains one or more Modules. It can be mapped to a complexType in XML Schema specification. | None. | None. |
| Module | XSDcomplexType | A Module is a stereotype describing the DICOM attributes within a DICOM Module. It is represented as a complexType in XML Schema specification. | None. | None. |
| Macro | XSDcomplexType | A Macro is a stereotype that describing a DICOM Macro. It is represented as a complexType in XML Schema specification. | None. | None. |
| Sequence | XSDcomplexType | A UML class with this stereotype represents a DICOM sequence attribute that contains a set of DICOM attributes. It is represented as a complexType in XML Schema specification. | codeId - a value indicates the DICOM tag of this sequence. codeMeaning - a string gives its DICOM name of this sequence. vr - a value indicates the value representation of DICOM sequence. Its default value is 'SQ'. | The class with this stereotype must be the destination of unidirectional association in the UML model. |
| SequenceItem | XSDcomplexType | A UML class with this stereotype represents a Sequence item within a Sequence. It is represented as a complexType in XML Schema specification. | None. | |
| Attribute | XSDcomplexType | A UML class with this stereotype represents a DICOM attribute. It is represented as a complexType in XML Schema specification. | codeId - same as above. codeMeaning - same as above. vr - same as above without default value. nillable - a Boolean indicates if the value of this attribute can be NULL or not. | None. |
| Datatype | XSDsimpleType | A Datatype is a stereotype describing a DICOM value representation. It is represented as a simpleType in XML Schema specification. | None. | These simpleTypes are derived from built-in types in XML Schema specification. |
| Enumeration (from UML profile for XML) | See Carlson, pp. 307. | This stereotype represents the defined terms or enumerated | See Carlson, pp. 307. | None. |

TABLE 5-continued

Summary of stereotype description of DICOM profile

| Stereotype | Base Class | Description | Tagged values | Constraints |
|---|---|---|---|---|
| XSDelement (from UML profile for XML) | See Carlson, pp. 309. | values of a DICOM Attribute. This stereotype represents the DICOM Attribute within a Module, Macro, or Sequence. | See Carlson, pp. 309. | None. |
| XSDattribute (from UML profile for XML) | See Carlson, pp. 309. | This stereotype represents the attributes (tag, DICOM name, DICOM type) of a DICOM Attribute. | See Carlson, pp. 309. | The attribute datatype may not refer to a class specification. |

For general purpose of UML modeling, the stereotypes defining the inventive profile for DICOM refer to the general stereotype base constructs such as Package, Component, and Class. The XML stereotype bases are referenced if the main objective is to generate XML schemas from UML construct models. To that end, OCL is a new notational language, a subset of the industry standard UML. OCL allows software architects, designers, and software developers to write constraints over the object models. In OCL, a constraint is a restriction on one or more values of an object-oriented model or system. There are three types of constraints defined in OCL: preconditions, postconditions, and invariants. Pre- and postconditions are defined for operations in objects. Invariant is a constraint that states a condition expressed in a mathematical expression that must always be met by all instances of a class, type, or interface. Constraints convey a number of benefits such as better documentation, improved precision, and communication without misunderstanding.

Following a set of syntaxes defined in OCL, various constraints can be put on attributes, operations, classes, and other types. FIG. 7 shows an example of putting an invariant constraint on an association. FIG. 7 is meant to communicate the constraint that a House can have a Cellar or a Basement, but it can't have both at the same time.

A Framework of Precise UML Modeling

A modeling framework for a DICOM IOD is shown in FIG. 8. First, naming conventions must be defined in order to keep a variety of construct names consistent. Second, how to model different 10 is discussed. Then the modeling rules for different DICOM constraints and finally, a way of expressing DICOM VRs is presented.

Naming Conventions

The following steps are required for maintaining consistency for construct names:
1. Change all the upper case letters to lower case.
2. Replace any blank space between two words with an underscore (_).
3. Remove apostrophes and brackets.
4. Replace hyphen (-) and slash (/) with underscore (_).
5. A string 'IE' is appended at the end of names for IE elements; 'Module' at the end of names for Module elements.
6. For class names or class type names, capitalize the first letter of each word.
7. 'Seq' is short for 'Sequence' in the class name; 'seq' in the referring class variable name; and 'seq_item' in the referred class variable name.

Packages and Namespace

To avoid repeat definitions of IEs, Modules, Sequences, Sequence Items, Macros, and atomic Attributes and also to reuse their definitions, a UML package associated with each IO type is created. For the current version of DICOM specification, IODs package contains 18 IODs (FIG. 8). FIG. 9 shows the UML package diagram of the DICOM information model that illustrates all the packages and their relationships.

Each package contains different types of IOs. DICOM IODs contains IOD classes, DICOM IEs contain IE classes, DICOM Modules contain Module classes, DICOM Sequences contain Sequence type classes, DICOM SequenceItems contain Sequence Item type classes, DICOM Macros contain Macro type classes, DICOM Attributes contain Attribute Type classes, DICOM Datatypes contain VR type classes, and DICOM Enumerations contain enumerated or defined terms.

Information Object Definitions

An example UML profile for DICOM that specifies the stereotypes for various DICOM IOs including IODs, IEs, Modules, Macros, Sequences, and Attributes has been introduced above. These stereotypes will be used for modeling different IOs. Therefore, an IOD is modeled as a IOD type, an IE as IE type, a Module as Module type, a Sequence as a Sequence type, a Sequence item as a SequenceItem type, a Macro as Macro type, and an Attribute as a Attribute type. Comprehensive DICOM SR IOD is one of three DICOM Document IODs which serve as an example of a UML model shown in FIG. 10.

It is clear to see that the IOD class is at the root level followed by IE classes and then Module classes. It also shows what is the base stereotype of each class and which package a class is derived from. Down to the Module level, for example, PatientModule, whose DICOM definition shown in Table 6, is represented as in FIG. 11. Table 6. Definition of Patient Module

| Attribute Name | Tag | Type | Attribute Description |
|---|---|---|---|
| Patient's Name | (0010,0010) | 2 | Patient's full name. |
| Patient ID | (0010,0020) | 2 | Primary hospital identification number or code for the patient. |
| Patient's Birth Date | (0010,0030) | 2 | Birth date of the patient. |
| Patient's Sex | (0010,0040) | 2 | Sex of the named patient. Enumerated Values: M = male |

-continued

| Attribute Name | Tag | Type | Attribute Description |
|---|---|---|---|
| | | | F = female |
| | | | O = other |
| Referenced Patient Sequence | (0008,1120) | 3 | A sequence which provides reference to a Patient SOP Class/Instance pair. Only a single Item shall be permitted in this Sequence. |
| >Referenced SOP Class UID | (0008,1150) | 1C | Uniquely identifies the referenced SOP Class. Required if Referenced Patient Sequence (0008,1120) is sent. |
| >Referenced SOP Instance UID | (0008,1155) | 1C | Uniquely identifies the referenced SOP Instance. Required if Referenced Patient Sequence (0008,1120) is sent. |
| Patient's Birth Time | (0010,0032) | 3 | Birth time of the Patient. |
| Other Patient IDs | (0010,1000) | 3 | Other identification numbers or codes used to identify the patient. |
| Other Patient Names | (0010,1001) | 3 | Other names used to identify the patient. |
| Ethnic Group | (0010,2160) | 3 | Ethnic group or race of the patient. |
| Patient Comments | (0010,4000) | 3 | User-defined additional information about the patient. |

Each DICOM Attribute is modeled as a variable member of the PatientModule class with a Class type associated with it. The stereotype of PatientModule class is Module. And the stereotype of each class member is XSDelement. The DICOM Macros are represented in the same way as the Modules. The only difference is that the stereotype base of the Macros is Macro (see Table 7 and FIG. 12).

TABLE 7

DICOM definition of Numeric Measurement Macro

| Attribute Name | Tag | Type | Attribute Description |
|---|---|---|---|
| Measured Value Sequence | (0040,A300) | 2 | This is the value of the Content Item. Zero or one Items shall be permitted in this sequence. |
| >Numeric Value | (0040,A30A) | 1 | Numeric measurement value. Only a single value shall be present. |
| >Measurement Units Code Sequence | (0040,08EA) | 1 | Units of measurement. Only a single Item shall be permitted in this sequence. |

>>Include 'Code Sequence Macro' Table 8.8-1
Defined Context ID is 82.

The DICOM Sequences are represented as Sequence typed classes with an XSDelement typed sequence item attribute and three XSDattribute typed auxiliary attributes: codeId, codeMeaning, and vr. Here vr takes the default value of 'SQ'. If a Sequence only contains a Macro, the sequence item is a type of Macro (see FIG. 13).

Actually, there is no Referenced SOP UID Macro defined in the current version of the DICOM specification. The author modeled 'referenced_sop_class_uid' (Referenced SOP Class UID) and 'referenced_sop_instance_uid' (Referenced SOP Instance UID) together as a Macro typed class named ReferencedSOPUID for convenience because these two DICOM Attributes are referred to many times as shown in Table 2.

If a Sequence contains more Attributes it will be a type of SequenceItem which represents all the Attributes within the Sequence, see Table 7 and FIG. 14. Because of the specific characteristics of DICOM data elements and structures, e.g., each DICOM Attribute with its own attributes such as name, DICOM Tag, Type, and description, each atomic Attribute is represented as a class that contains not only its data element but also its attributes. This approach is taken mainly to help automate the generation of XML schemas (see FIG. 15).

Constraints

The constraints in the DICOM information model are represented as a type of invariant constraint. They can be put on attributes or associations. FIG. 16 shows a sample UML diagram of Document Content Macro with OCL constraints.

As shown above, the multiplicity of date time is [0 . . . 1]. Based on its DICOM description in Table 1, it shows that it is required if Value Type (0040,A040) is DATETIME. An Invariant constraint is put to express this constraint as shown in FIG. 16 and highlighted in FIG. 17. However, some DICOM constraints cannot be represented using Invariant constraint such as the condition for Specimen Identification Module.

Types of Data Elements

Five Types of data elements are defined in . They are Type 1, Type 1C, Type 2, Type 2C, and Type 3, where two parameters combined together express this kind of constraint, shown in Table 8.

TABLE 8

Representation of Types of data elements

| | Multiplicity | Value of nillable attribute |
|---|---|---|
| Type 1 | 1 | False |
| Type 1C | 0 . . . 1 | False |
| Type 2 | 1 | True |
| Type 2C | 0 . . . 1 | True |
| Type 3 | 0 . . . 1 | True |

The SOP Common Module is an example (Table 9) which shows the first two Attributes are Type 1, the third Type 1C, and the rest type 3.

TABLE 9

Part of SOP Common Module

| Attribute Name | Tag | Type | Attribute Description |
|---|---|---|---|
| SOP Class UID | (0008,0016) | See C.12.1.1.1 | Uniquely identifies the SOP Class. See PS 3.4. |
| SOP Instance UID | (0008,0018) | See C.12.1.1.1 | Uniquely identifies the SOP Instance. See PS 34. |
| Specific Character Set | (0008.0005) | 1C | Character Set that expands or replaces the Basic Graphic Set. Required if an expanded or replacement character set is used. See C.12.1.1.2 for Defined Terms. |
| Instance Creation Date | (0008,0012) | 3 | Date the SOP Instance was created. |
| Instance Creation Time | (0008,0013) | 3 | Time the SOP Instance was created. |
| Instance Creator UID | (0008,0014) | 3 | Uniquely identifies device which created the SOP Instance. |

FIG. 18 shows that SOP Class UID and SOP Instance UID are Type 1 so that the multiplicity of sop_class_uid and sop_instance_uid is 1 and their nillable attributes take the default value, false, based on the stereotype of Attribute. Specific Character Set is a Type 1C in that the multiplicity of specific_character_set is [0 . . . 1] in SOPCommonModule class and the nillable attribute takes a value of true. This is also true for the Type 3 data elements such as Instance Creator UID Attribute.

Value Representations

In the current version of the DICOM specification there are 26 VRs defined. Each of them has different constraints or patterns which can be expressed in the OCL notation language. FIG. 19 gives the UML representation (Table 4) of a subset of VRs. The AS—Age string as described in Table 4, is represented to be a Class inherited from string Type with a pattern of '[0-9] {3} [DWMY]'. MaxLength restricts the length of string AE and CS to 16 bytes.

Enumerated Values and Defined Terms

There are two ways to represent enumerated values or defined terms. One is to use the 'enum' OCL type to list all the enumerated values as shown in FIG. 20. The other is to use stereotype enumeration as shown in FIG. 21 The latter is good for more than two enumerated items.

Sample Modeling: A UML Model for Comprehensive DICOM IOD

Based on the above framework, a UML model of comprehensive DICOM IOD was created. The UML model of comprehensive DICOM IOD captures all the IEs, Modules, Macros, Sequences, and Attributes including various constraints, data structures, DICOM tags, and DICOM VRs. FIGS. 22-31 highlight DICOM the UML class diagrams of the Modules of DICOM Comprehensive DICOM IOD and DICOM VRs. Such a model assists system architects and developers in understanding the DICOM information model. Also, XML schemas can be easily generated using XMI from this model, which will not be addressed in this document. The UML models for other DICOM IODs can also be built based on this modeling framework. Some common Modules such as Patient, General Study, and SOP Common can be reused.

There are three data types related to date or time in the DICOM specification: DA, DT, and TM. They are of string type with different constraints. There is no problem in representing these constraints using regular expressions. But the issue is the date representation from DICOM specification is different from that of the XML Schema specification which conforms to the ISO definition. Take date as an example; the format from ISO is 'CCYY-MM-DD' (where CC—century, YY—year, MM—month, and DD—day) and the format from DICOM is 'CCYYMMDD'. This makes it inconvenient to represent DICOM date in XML format and other programming languages. It would be better to modify the DICOM DA, DT, and TM representation so that they are consistent with ISO date and time format.

Unexpressed Constraints

Most of the DICOM constraints can be expressed in OCL. However, a few of them cannot be expressed. Take a Type 1C data element, Verifying Observer Sequence as an example, it is required only if the Verification Flag has the value of VERIFIED. In this case, both Verifying Observer Sequence and Verification Flag are DICOM Attributes, and also Verification Flag has known values, which can be expressed in OCL, as shown in FIG. 32. On the other hand, some conditions cannot be expressed in OCL expressions, for example the condition of requiring Specimen Identification in Table 1 is if the Observation Subject is a Specimen. It cannot be represented in a UML diagram because there is no definition of Observation Subject in the DICOM information model. We proposed a temporary constraint—Other, to express these constraints which cannot be expressed in Invariant, Post- and Precondition, see FIG. 33. This is an open issue to the DICOM information model.

The foregoing merely illustrates the principles of the invention. It will thus be appreciated that those skilled in the art will be able to devise various arrangements which, although not explicitly described or shown herein, embody the principles of the invention and are thus within the spirit and scope of the following claims.

What is claimed is:

1. A method for converting an electronic DICOM document into an electronic UML document utilizing a constrained UML profile, the method comprising the acts of:
converting each DICOM Information Entity in the DICOM document into a corresponding UML class in the UML document utilizing a naming convention based on a name of each DICOM Information Entity converted,
converting each DICOM IOD Module in the DICOM document into a corresponding UML class in the UML document utilizing a naming convention based on a name of each DICOM IOD Module converted,
converting each DICOM Macro in the DICOM document into a corresponding UML class in the UML document utilizing a naming convention based on a name of each DICOM Macro converted,
converting each DICOM Attribute in the DICOM document into a corresponding UML attribute in the UML document utilizing a naming convention based on a name of each DICOM Attribute converted, each act of converting based on the constrained UML profile, and
providing the electronic UML document, based on results from the converting acts, to at least one of a user, a storage device, and a UML processing system for processing.

2. The method as claimed in claim 1, wherein converting each DICOM Information Entity comprises the act of converting
each DICOM Information Entity into the corresponding UML class with a class name that corresponds to the Information Entity name.

3. The method as claimed in claim 1, wherein converting each DICOM IOD Module comprises the act of converting
each DICOM IOD Module into the corresponding UML class with a class name that corresponds to the module name modified to remove space characters if present in the module name.

4. The method as claimed in claim 1, wherein converting each DICOM IOD Module comprises the act of converting
each DICOM Macro name having a "Macro" postfix into the corresponding UML class with a class name that corresponds to the macro name modified to remove the "Macro" postfix.

5. The method as claimed in claim 1, where in
each DICOM Sequence has a name, the method comprising the act of converting each DICOM Sequence into a corresponding UML class with a UML class name that corresponds to a Sequence name, wherein the UML class has two UML attributes in XSDattribute stereotype representing a DICOM tag and a DICOM name of each DICOM Sequence based on the constrained UML profile.

6. The method as claimed in claim 1, wherein converting each DICOM Attribute comprises the act of converting
each DICOM Attribute into the corresponding UML attribute with a UML attribute name that corresponds to the DICOM Attribute name, modified to replace each upper case letter in the DICOM Attribute name with a corresponding lower case letter, modified to replace each blank space in the DICOM Attribute name with an underscore character, modified to replace each hyphen character in the DICOM Attribute name with an underscore character, modified to remove each apostrophe character from the DICOM Attribute name, modified to remove each bracket character from the DICOM Attribute name, and, each UML attribute has its associated types capturing its DICOM type, DICOM tag, and DICOM Name.

7. A computer program, stored on a computer readable medium, the computer program configured to be executed on a computer system and is configured to receive a DICOM document and produce a UML document by the method of claim 1.

8. A method for electronically converting a DICOM atomic attribute into a UML class attribute utilizing a constrained UML profile, the method comprising the acts of:

copying each lower case letter from the atomic attribute to the class attribute, converting each upper case letter from the atomic attribute to a corresponding lower case letter of the class attribute, converting each blank space from the atomic attribute to an underscore character of the class attribute, converting each hyphen character from the atomic attribute to an underscore character of the class attribute, and providing the UML class attribute, based on results from the converting acts, to at least one of a user, a storage device, and a UML processing system for processing.

9. A DICOM to Object-Oriented-representation converter stored in a memory, comprising:

an DICOM document to UML document converter that is configured convert an electronic DICOM document into an electronic UML document utilizing a constrained UML package, the converter further configured to:

convert each DICOM Information Entity in the DICOM document into a corresponding UML class in the UML document utilizing a naming convention based on a name of each DICOM Information Entity converted, convert each DICOM IOD Module in the DICOM document into a corresponding UML class in the UML document utilizing a naming convention based on a name of each DICOM IOD Module converted, convert each DICOM Macro in the DICOM document into a corresponding UML class in the UML document utilizing a naming convention based on a name of each DICOM Macro converted, convert each DICOM Attribute in the DICOM document into a corresponding UML attribute in the UML document utilizing a naming convention based on a name of each DICOM Attribute converted, wherein the converting is based on the constrained UML package, and provide the electronic UML document, based on results of the converting, to at least one of a user, a storage device, and a UML processing system for processing.

10. The converter of claim 9, wherein each UML atomic attribute is converted from a corresponding DICOM Element with four attributes: coding_scheme, code_id, type, and value.

11. The converter of claim 9, further comprising:

a UML document to DICOM document converter that is configured to:

map each UML class in the UML document into a corresponding DICOM DTD element.

map each UML class attribute in the UML document into a corresponding DICOM DTD element, map each UML association and uses relationship in the UML document into a corresponding DICOM DTD element, and map each UML atomic attribute class in the UML document into a corresponding DICOM element.

12. The converter of claim 11, wherein the DICOM document to UML document converter is further configured to:

convert each DICOM recursive element into a corresponding pair of UML elements that reference each other.

* * * * *